(12) United States Patent
Bressan et al.

(10) Patent No.: US 7,803,854 B2
(45) Date of Patent: Sep. 28, 2010

(54) PLANT PR-5 PROTEINS AS MAMMALIAN THERAPEUTIC AGENTS

(75) Inventors: Ray A. Bressan, W. Lafayette, IN (US); Meena L. Narasimhan, W. Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 132 days.

(21) Appl. No.: 12/005,333

(22) Filed: Dec. 26, 2007

(65) Prior Publication Data

US 2009/0018065 A1 Jan. 15, 2009

Related U.S. Application Data

(62) Division of application No. 11/234,115, filed on Sep. 26, 2005, now abandoned.

(60) Provisional application No. 60/613,647, filed on Sep. 27, 2004, provisional application No. 60/657,335, filed on Feb. 28, 2005.

(51) Int. Cl.
C07K 14/00 (2006.01)

(52) U.S. Cl. .......................................... 524/2; 530/350

(58) Field of Classification Search ........................ None
See application file for complete search history.

(56) References Cited

OTHER PUBLICATIONS

Yamauchi et al. 2003. Globular adiponectin protected ob/ob mice from diabetes and ApoE-deficient mice from atherosclerosis. J. Biol. Chem. 278: 2461-2468.*

Anzlovar, S., Serra, M.D., Dermastia, M., and Menestrina, G. (1998). Membrane permeabilizing activity of pathogenesis-related protein linusitin from flax seed. Mol. Plant-Microbe Interact. 11, 610-617.

Becker and Guarente, "High-Efficiency Transformation of Yeast by Electroporation" Methods in Enzymology 194:182-187 (1991).

Brakenhielm, E., Veitonmaki, N., Cao, R., Kihara, S., Matsuzawa, Y., Zhivotovsky, B., Funahashi, T., Cao, Y. (2004). Adiponectin-induced antiangiogenesis and antitumor activity involve caspase-mediated endothelial cell apoptosis. Proc. Natl. Acad. Sci. USA 101: 2476-2481.

H. Breiteneder, C. Ebner, "Molecular and biochemical classification of plant-derived food allergens," J. Allergy Clin. Immunol. 106(Jul. 2000): 27-36.

David, N.E., Gee, M., Andersen, B., Naider, F., Thorner, J. and Stevens, R.C. (1997) Expression and purification of the Saccharomyces cerevisiae α-factor receptor (Ste2p), a 7-Transmembrane-segment G protein-coupled receptor. J. Biol. Chem., 272, 15553-15561.

Diez JJ, Iglesias P: The role of the novel adipocyte-derived hormone adiponectin in human disease. Eur J. Endocrinol 148: 293-300, 2003.

S. T. Ding, B. H. Liu, and Y. H. Ko: Cloning and expression of porcine adiponectin and adiponectin receptor 1 and 2 genes in pigs. J Anim Sci, Nov. 1, 2004; 82(11): 3162-3174.

Eck M. J., Sprang S. R. The structure of tumor necrosis factor—α at 2.6 Å resolution: implications for receptor binding. J. Biol. Chem., 264: 17595-17605, 1989.

Elble, R., "A Simple and Efficient Procedure for Transformation of Yeasts", BioTechniques, 1992, 13, 18-20.

Forsberg, H., and Ljungdahl, P.O. ((2001).). Sensors of extracellular nutrients in Saccharomyces cerevisiae. Curr. Genet. 40, 91-109.

Fruebis, J. et al., "Proteolytic Cleavage Product of 30-kDa Adipocyte Complement-Related Protein Increases Fatty Acid Oxidation in Muscle and Causes Weight Loss in Mice", PNAS, Feb. 13, 2001, pp. 2005-2010, vol. 98, No. 4.

Gimeno, C.J., Ljungdahl, P.O., Styles, C.A., and Fink, G.R. (1992). Unipolar cell divisions in the yeast S. cerevisiae lead to filamentous growth: regulation by starvation and RAS. Cell 68, 1077-1090.

Hampsey, "A Review of Phenotypes in Saccharomyces cerevisiae," Yeast 13:1099 1133 (1997).

Harashima T, Heitman J: The Galpha protein Gpa2 controls yeast differentiation by interacting with kelch repeat proteins that mimic Gbeta subunits. Mol Cell 2002, 10(1): 163-173.

Herskowitz, I., Jensen, J.E. 1991. Putting the HO gene to work: practical uses for mating-type switching. Methods Enzymol. 194:132-146.

Ibeas JI, Lee H, Damsz B, Prasad DT, Pardo JM, Hasegawa PM, Bressan RA, Narasimhan ML: Fungal cell wall phosphomannans facilitate the toxic activity of a plant PR-5 protein. Plant J 2000, 23:375-383.

Ibeas, J.I., Yun, D. -J., Damsz, B., Narasimhan, M.L., Uesono, Y., Ribas, J.C., Lee, H., Hasegawa, P.M., Bressan, R.A., and Pardo, J.M. (2001). Resistance to the plant PR-5 protein osmotin in the model fungus Saccharomyces cerevisiae is mediated by the regulatory effects of SSD1 on cell wall composition. Plant J. 25, 271-280.

Jazwinski SM, 1999. The RAS genes: a homeostatic device in Saccharomyces cerevisiae longevity. Neurobiol Aging 20: 471-478.

Jones, E.Y., et al., "Structure of tumour necrosis factor," Nature, 338: 225-228 (1989).

R: Kaneko and N. Kitabatake: Structure-Sweetness Relationship in Thaumatin: Importance of Lysine Residues, Chem Senses, Feb. 1, 2001; 26(2): 167-177.

(Continued)

Primary Examiner—Karen Cochrane Carlson
(74) Attorney, Agent, or Firm—Barnes & Thronburg LLP; Alice O. Martin

(57) ABSTRACT

The Proteins of the PR-5 family having a lectin-like β barrel domain control apoptosis in yeast through receptor binding. Receptors that specifically bind to PR-5 proteins having a lectin-like β barrel domain have been found to be homologous to mammalian adiponectin receptors, and such PR-5 proteins can act as functional homologues of adiponectin and control adiponectin response in mammals. PR-5 proteins having a lectin-like β barrel domain, for example osmotin, can be used in the treatment of conditions in mammals which are the result of activation or inhibition of adiponectin receptor-mediated metaboloic pathways. PR-5 proteins having a lectin-like β barrel domain, nucleic acids encoding such proteins, and receptors that specifically bind such proteins, can also be used in screening and rational design of new therapeutic agents for use in mammals.

9 Claims, 5 Drawing Sheets

OTHER PUBLICATIONS

I. V. Karpichev, L. Cornivelli, and G. M. Small, Multiple Regulatory Roles of a Novel *Saccharomyces cerevisiae* Protein, Encoded by YOL002c, in Lipid and Phosphate Metabolism. J. Biol. Chem., May 24, 2002; 277(22): 19609-19617.

Karpusas et al., "A crystal structure of an extracellular fragment of human CD40 ligand," Structure (Oct. 1995) 3(10): 1031-1039.

Kubota, N., et al. 2002. Disruption of adiponectin causes insulin resistance and neointimal formation. *J. Biol. Chem.* 277:25863-25866.

Xiadong LI, et al., "Human Receptors for Sweet and umami taste", Proceeding of the National Academy of Science, vol. 99, No. 7, p. 4692-4696, Apr. 2, 2002.

Liu, H., J. Krizek, and A. Bretscher. 1992. Construction of a GAL1-regulated yeast cDNA expression library and its application to the identification of genes whose overexpression causes lethality in yeast. Genetics 132:665-673.

Lyons, T. J., Villa, N. Y., Regalla, L. M., Kupchak, B. R., Vagstad, A., Eide, D. J. (2004). Metalloregulation of yeast membrane steroid receptor homologs. *Proc. Natl. Acad. Sci. USA* 101: 5506-5511.

Min et al.: Crystal structure of osmotin, a plant antifungal protein, Proteins (2004); 54(1):170-173.

BC Monk, C Montesinos, C Ferguson, K Leonard, and R Serrano: Immunological approaches to the transmembrane topology and conformational changes of the carboxyl-terminal regulatory domain of yeast plasma membrane H(+)-ATPase, (1991) J. Biol. Chem. 266: 18097-18103.

Mumberg et al., "Yeast vectors for the controlled expression of heterolgous proteins in different genetic backgrounds," *Gene*. 156:119-122, 1995.

Narasimhan et al. (2001), A plant defense response effector induces microbial apoptosis. Mol. Cell 8, 921-930.

Narsimhan et al., (2003) Overexpression of a cell wall glycoprotein in *Fusarium oxysporum* increases virulence and resistance to a plant PR-5 protein. Plant Jour. 36: 390-400.

Nicholls, A. et al., (1991), "Protein Folding and Association: Insights From the Interfacial and Thermodynamic Properties of Hydrocarbons," Proteins, Structure, Function and Genetics, 11:281-296.

Robzyk K; Kassir Y. (1992) A simple and highly efficient procedure for rescuing autonomous plasmids from yeast. Nucleic acids research; 20(14):3790.

Rolland F, Winderickx J, Thevelein JM: Glucose-sensing and signaling mechanisms in yeast. *FEMS Yeast Res* 2002, 2:183-201.

Scherer, P.E., et al., "A Novel Serum Protein Similar to C1q, produced Exclusively in Adipocytes", Journal of Biological Chemistry, 270:26746-26749 (1995).

Shapiro et al., The crystal structure of a complement-1q family protein suggests an evolutionary link to tumor necrosis factor. *Curr Biol* 1998. 8:335-338.

Sherman F. Getting started with yeast. *Methods Enzymol.* 1991; 194:3-21.

Stanhill, N. Schick, and D. Engelberg: "The Yeast Ras/Cyclic AMP Pathway Induces Invasive Growth by Suppressing the Cellular Stress Response," Mol. Cell. Biol., Nov. 1, 1999; 19(11): 7529-7538.

P. Veronese, M. T. Ruiz, M. A. Coca, A. Hernandez-Lopez, H. Lee, J. I. Ibeas, B. Damsz, J. M. Pardo, P. M. Hasegawa, R. A. Bressan, et al. (2003): "In Defense against Pathogens. Both Plant Sentinels and Foot Soldiers Need to Know the Enemy," *Plant Physiology* 131, 1580-1590.

Wach, A., Brachat, A., Alberti-Segui, C., Rebischung, C., and Philippsen, P. (1997): Heterologous HIS3 marker and GFP reporter modules for PCR-targeting in *Saccharomyces cerevisiae*. Yeast 13, 1065-1075.

Weickmann, J.L., Blair, L. C, and Wilcox, G.L. (1994) High level expression of thaumatin in *Saccharomyces cerevisiae*. In Thaumatin, M. Witty and J.D. Higginbotham, eds. (Boca Raton: CRC Press) pp. 151-169.

Weis, et al., "Trimeric Structure of a C-type Mannose-binding Protein," *Structure* 2(12): 1227-1240 (1994).

Yamauchi, T, et al. The fat-derived hormone adiponectin reverses insulin resistance associated with both lipoatrophy and obesity. *Nat. Med.* 2001. 7:941-946.

Yamauchi T, Waki H, Kamon J, Murakami K, Motojima K, Komeda K et al. Inhibition of RXR and PPAR γ ameliorates diet-induced obesity and type 2 diabetes. *J Clin Invest* 2001; 108: 1001-1013.

Yamauchi T et al.: "Cloning of adiponectin receptors that mediate antidiabetic metabolic effects," Nature 423(6941): 762-769 (2003).

Yun, D. J., J. I. Ibeas, H. Lee, M. A. Coca, M. L. Narasimhan, Y. Uesono, P. M. Hasegawa, J. M. Pardo, and R. A. Bressan: (1998) "Osmotin, a plant antifungal protein, subverts signal transduction to enhance fungal cell susceptibility." Mol. Cell 1:807-817.

Yun, D.-J., Y. Zhao, J.M. Pardo, M.L. Narasimhan, B. Damsz, H. Lee, L.R. Abad, M.P. D'Urzo, P.M. Hasegawa, R.A. Bressan: (1997) "Stress proteins on the yeast cell surface determine resistance to osmotin, a plant antifungal protein," PNAS 94:7082-7087.

Zhou, Z., Gartner, A., Cade, R., Ammerer, G., and Errede, B.: (1993) "Pheromone-induced signal transduction in Saccharomyces cerevisiae requires the sequential function of three protein kinases," Mol. Cell. Biol. 13, 2069-2080.

Hancock, R. E, and Scott, M. G. (2000). The role of antimicrobial peptides in animal defenses. Proc. Natl. Acad. Sci. USA. 97:8856-8861.

\* cited by examiner

PLANT PR-5 PROTEINS AS MAMMALIAN THERAPEUTIC AGENTS

CROSS REFERENCE TO RELATED APPLICATIONS

This application is a divisional of and claims priority under 35 U.S.C. §119 from U.S. application Ser. No. 11/234,115, filed Sep. 26, 2005, now abandoned, which claims priority under 35 U.S.C. §119 from U.S. provisional patent application Ser. No. 60/613,647, filed Sep. 27, 2004 and Ser. No. 60/657,335, filed Feb. 28, 2005 and which are incorporated herein in their entirety by reference.

STATEMENT REGARDING FEDERALLY SPONSORED RESEARCH OR DEVELOPMENT

This invention was made with U.S. Government support under Contract No. 0350439-MCB awarded by the National Science Foundation. The government has certain rights in this invention.

REFERENCE TO SEQUENCE LISTING

The present application incorporates by reference a file named 1499F-007DIV1 Bressan sequences.ST25.txt including SEQ ID NO:1 to SEQ ID NO:3, provided in a computer readable form and filed with the present application as well as with U.S. application Ser. No. 11/234,115. The sequence listing recorded on the CD-ROM is identical to the written (on paper) sequence listing provided herein.

TECHNICAL FIELD

The present invention relates to the treatment of mammalian disorders, specifically disorders of glucose and lipid metabolism, to therapeutic agents for the treatment of such conditions, and to the design and/or identification of such therapeutic agents.

BACKGROUND OF THE INVENTION

Among families of antimicrobial proteins associated with plant defense are the pathogenesis related proteins of family 5 (PR-5) that are structurally related to the sweet tasting protein thaumatin (Veronese et al., 2003). PR-5 proteins are distinguished by having (a) a three domain structure consisting of a β barrel (Domain I) that forms the compact core of the molecule (this structure is commonly found in lectins and is hereafter referred to as a "lectin-like β barrel"); a domain (Domain II) that extends from Domain I and consists of several loops stabilized by four disulfide bonds; and Domain III that also extends from domain I and consists of a small loop stabilized by two disulfide bonds, (b) an alanine commonly located at the cleavage site of the N-terminal leader sequence, (c) up to 16 cysteine residues that have a conserved spatial distribution throughout the protein and linked by disulfide bridges (Min, et al., 2004), and (d) a cleft formed by Domains I & II that could be associated with biological activity.

Osmotin is an antifungal tobacco PR-5 protein. It induces programmed cell death in *S. cerevisiae* by signaling suppression of cellular stress responses via RAS2/cAMP (Narasimhan et al., 2001). Most of the PR-5 proteins, including osmotin, have specific wide-spectrum antifungal activities, suggesting that target recognition may be determined by their interaction with pathogen cell surface components. In the case of osmotin, specific fungal cell wall components enhance or suppress osmotin antifungal activity (Narasimhan et al., 2003; Veronese et al., 2003). In *S. cerevisiae*, the PIR family of cell wall glycoproteins are osmotin-resistance determinants (Yun et al., 1997). Phosphomannans of yeast cell wall glycoproteins have been reported to increase osmotin toxicity, probably by serving as docking structures for osmotin, thereby increasing its local concentration and diffusion across the cell wall (Ibeas et al., 2000). Genetic analyses have revealed that SSD1, a protein that affects cell wall morphogenesis and deposition of PIR proteins, is a determinant of resistance to osmotin (Ibeas et al., 2001). Unidentified changes in the yeast cell wall that enhance toxicity are induced by osmotin via activation of a mitogen-activated protein kinase cascade (Yun et al., 1998). Specific interactions at the plasma membrane also appear to be required for osmotin antifungal activity because yeast spheroplasts that are susceptible to tobacco osmotin can be resistant to PR-5 proteins from other plant species (Yun et al., 1997). Although the best studied role of PR-5 proteins is their antifungal activity, a signaling or recognition role has been suggested. Veronese et al., 2003

Adiponectin (also called 30-kDa adipocyte complement-related protein-Acrp30) is an antidiabetic and antiatherosclerotic protein hormone in mammals that conditions sensing of energy status, fatty acid oxidation and glucose transport upon interaction with adiponectin receptors. Known adiponectin receptors include the human AdipoR1 and AdipoR2 (Diez and Iglesias, 2003; Yamauchi et al., 2003a,b), and the pig adiponectin receptor genebank NM_001007193) (Ding et al. 2004). Additional adiponectin receptor sequences can be found in GeneBank. Serum adiponectin levels are decreased under conditions of obesity, insulin resistance, and type II diabetes (Yamauchi, et al., 2003a), while administration of adiponectin lowers serum glucose levels and ameliorates insulin resistance in mice (Yamauchi, et al. 2003a). The mammalian adiponectin receptors AdipoR1 and AdipoR2 are predicted to have seven transmembrane domains, a characteristic feature of G protein-coupled receptors (GPCRs).

SUMMARY OF THE INVENTION

Proteins of the PR-5 family control apoptosis in yeast through receptor comprising seven transmembrane domains, a characteristic of GPCRs. Receptors which specifically bind to PR-5 proteins have been found to be homologous to mammalian adiponectin receptors, and PR-5 proteins can act as functional homologues of adiponectin and control adiponectin response in mammals.

A plasma membrane determinant of osmotin sensitivity in yeast cells was isolated, after being identified by its ability to confer an osmotin supersensitive phenotype upon gene overexpression. The gene, ORE20/PHO36, encodes a seven transmembrane domain receptor-like protein (PHO36), having structural homology to GPCRs, and significant sequence identity (29%) to mammalian adiponectin receptor R1. PHO36 regulates yeast lipid and phosphate metabolism, and is required for full sensitivity to osmotin in yeast. PHO36 functions upstream of RAS2 in the osmotin-induced apoptotic pathway. A mammalian homolog of PHO36 is a receptor for the hormone adiponectin, which regulates cellular lipid and sugar metabolism. While the osmotin receptor PHO36 and adiponectin receptors share significant sequence homology, osmotin and adiponectin, the corresponding receptor-binding proteins, do not share sequence similarity (≦10% homology). However, the tertiary structures of a lectin-like β barrel domain of both proteins have been found to be very similar and can be overlapped. It has been found that osmotin can bind selectively to mammalian adiponectin receptors, and acts as an adiponectin agonist in mammalian systems.

Thus, osmotin, and related proteins in the PR-5 family having a structurally homologous lectin-like β barrel domain, suitably formulated in a pharmaceutically acceptable carrier, can be used as therapeutic agents for the treatment of a wide variety of mammalian disorders in which adiponectin receptor-mediated pathways are implicated. Such disorders include diabetes, arteriosclerosis, and heart disease. Osmotin, and related PR-5 proteins having a structurally homologous lectin-like β barrel domain, can also be used as surrogates for adiponectin in the development of therapeutic methods for treatment of mammalian disorders in which adiponectin receptor-mediated pathways are implicated. Osmotin, and related PR-5 proteins having a structurally homologous lectin-like β barrel domain, can also be used as a basis for the rational design of new therapeutic agents for the treatment of mammalian disorders in which adiponectin receptor-mediated pathways are implicated.

Receptors to which osmotin, and related PR-5 proteins having a structurally homologous lectin-like β barrel domain, can specifically bind (for example the yeast receptor PHO36) can be used as screening systems for new therapeutic agents useful in the treatment of mammalian disorders in which adiponectin receptor-mediated pathways are implicated. Such screening methods can be carried out using a preparation of the isolated receptor (e.g., in solution, or bound for use in a column packing, thin-layer plate, or micro-array), or using a cell line or tissue culture in which the receptor is expressed.

The yeast strain BWG7a expresses the osmotin receptor PHO36 and is sensitive to osmotin. When caused to over-express PHO36, this yeast strain was found to be supersensitive to the apoptosis-inducing effects of osmotin. A cell, such as the yeast strain BWG7a or any other suitable cell line expressing or over-expressing PHO36 or similarly sensitive PR-5 protein receptors, may thus be used as a primary screen to identify chemical and protein/peptide agonists or antagonists of adiponectin receptor function in mammals. This screen allows identification of potential adiponectin receptor-mediated therapeutic agents. In a preferred embodiment, the cell is one that over-expresses PHO36 or similarly sensitive PR-5 receptor.

A nucleic acid having the osmotin genomic sequence [SEQ ID NO. 1] or cDNA sequence [SEQ ID NO. 2], or their protein products and therapeutic products derived therefrom, or derivatives and functional homologues thereof, can be used in structure/function analyses of adiponectin receptor binding, in order to improve the efficacy of adiponectin, PR-5 proteins, or derivatives or functional homologues thereof, as therapeutic agents. Such structure/function analyses can include comparative analyses using in vitro molecular evolution approaches, such as DNA shuffling, or enhanced selective mutagenesis and phage display or other selective methods for improved peptide function, and rational design approaches to develop improved therapeutic agents, including drugs that are agonists or antagonists of all or part of the adiponectin targets in human cells.

One embodiment of the invention is a pharmaceutical composition comprising a PR-5 protein having a lectin-like, barrel domain. In a preferred embodiment, the PR-5 protein is osmotin [SEQ ID NO. 3], or a homolog thereof having a lectin-like β barrel domain.

Another embodiment of the invention is a method for treating a mammal suffering from a disorder that is the result of activation or inhibition of a metabolic pathway mediated by adiponectin or an adiponectin-like protein, comprising administration of a PR-5 protein having a lectin-like β barrel domain. In preferred embodiments the disorder is selected from the group consisting of type II diabetes, insulin resistance, hyperlipidemia, arteriosclerosis, and heart disease. In more preferred embodiments, the method comprises administration of osmotin [SEQ ID NO. 3], or a homolog of osmotin having a lectin-like β barrel domain.

Another embodiment of the invention is the use of a PR-5 protein in the rational design of a therapeutic agent that is an agonist or an antagonist of all or part of the adiponectin targets in a mammalian cell. In a preferred embodiment the therapeutic agent is an agonist. In another preferred embodiment, the therapeutic agent is an antagonist. In a more preferred embodiment, the rational design includes structure/function analysis. In a most preferred embodiment, the PR-5 protein is osmotin [SEQ ID NO: 3].

Another embodiment of the invention is the use of a nucleic acid sequence that encodes a PR-5 protein having a lectin-like β barrel domain in the rational design of a therapeutic agent that is an agonist or antagonist of all or part of the adiponectin targets in a mammalian cell. In a preferred embodiment, the therapeutic agent is an agonist. In another preferred embodiment, the therapeutic agent is an antagonist. In a more preferred embodiment, the rational design includes structure/function analysis, preferably structure/function analysis includes one or more technique selected from the group consisting of DNA shuffling, enhanced selective mutagenesis and phage display. In the most preferred embodiments, the nucleic acid sequence is SEQ ID NO. 1 or SEQ ID NO. 2.

Another embodiment of the invention is the use of a receptor protein, having specific binding affinity for a PR-5 protein having a lectin-like β barrel domain, as a primary screen to identify a therapeutic agent that is an agonist or an antagonist of all or part of the adiponectin targets in a mammalian cell. In one preferred embodiment the screen is carried out using a receptor that is in isolated form. In another preferred embodiment, the screen is carried out using a cell line or tissue culture expressing the receptor, more preferably overexpressing the receptor. A preferred cell line for use in this embodiment is a yeast cell line, most preferably a yeast cell line overexpressing the receptor. The most preferred PR-5 receptor for use in this embodiment is PHO36.

DETAILED DESCRIPTION

Figure 1:
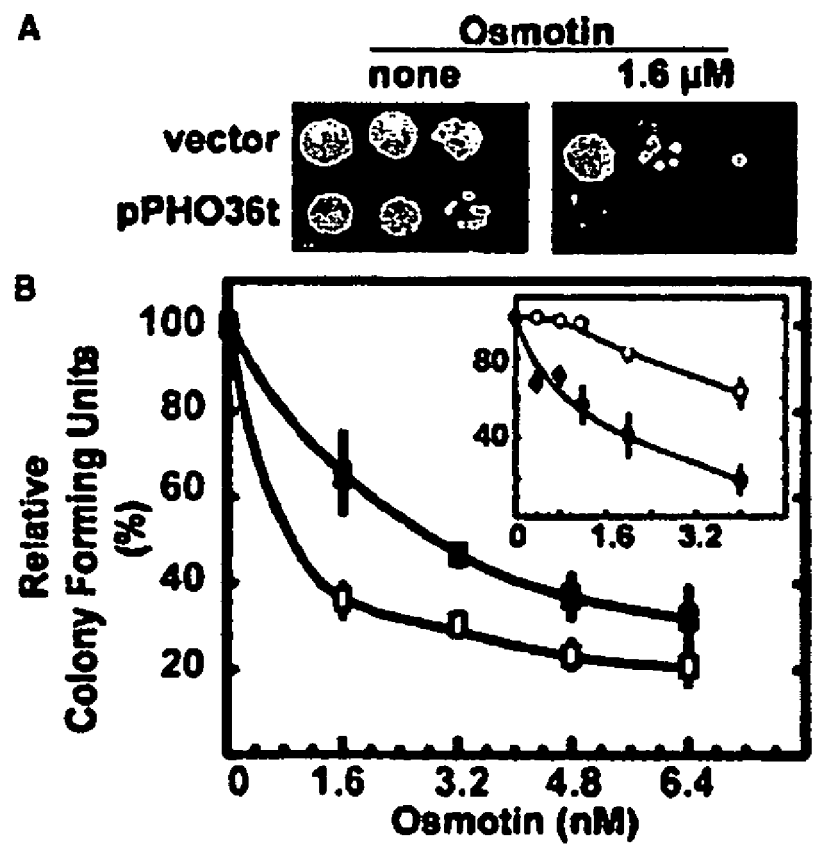
FIG. 1: PHO36 Mediates Sensitivity to Osmotin in Yeast. A. Aliquots (2.5 μl) of 10-fold serial dilutions of log phase cultures ($A_{600nm}$ 0.4) of the yeast strain BWG7a transformed with the centromeric plasmid pRS316 without (vector) or with PHO36t insert (pPHO36t) were spotted on selective SC-galactose media without (none) or with osmotin supplement (1.6 μM) and allowed to grow for 3 days at 28° C. B. Spheroplasts ($10^6$ ml$^{-1}$) derived from the wild-type strain BWG7a (□) or the isogenic Δpho36 mutant (■) were diluted and plated on YPD agar containing 0.8 M sorbitol and the indicated concentrations of osmotin. Viable spheroplasts were counted after 3 days incubation at 28° C. Viable counts are normalized to the value without added osmotin. Values are the average of three different experiments ±SE (inset). The results of a similar experiment with spheroplasts of BWG7a strain carrying the plasmid pRS316 without (○) or with PHO36t insert (pPHO36t;●), performed in selective SC-galactose media supplemented with 0.8 M sorbitol, are shown.

Homology of the PR-5 and Adiponectin Receptor-Ligand Systems. The genomic sequence of PHO36 encodes a polypeptide with seven putative transmembrane domains that localizes to the cell plasma membrane, the only hallmarks conserved among GPCRs. PHO36 has been inferred to have a regulatory role in lipid, phosphate and zinc metabolism because (a) PHO36 expression is induced by phosphate, the $C_{14:0}$ fatty acid, myristate and the oleate-dependent transcription factors OAF1 and PIP2, (b) various genes involved in fatty acid metabolism and phosphate signaling in yeast are induced in a pho36 mutant, (c) the pho36 mutant has high levels of acid phosphatase and accumulated polyphosphate in vacuoles, (d) the Δpho36 mutant is resistant to the sterol-binding antibiotic nystatin, (e) the Δpho36 mutant grows poorly on glycerol plus myristate as a carbon source (Karpichev et al., 2002), and (f) PHO36 expression is controlled by zinc levels in the growth medium and by the transcription factor ZAP1 that senses zinc deficiency (Lyons et al., 2004). It has now been found that osmotin interacts with PHO36 and affects its natural function: (a) PHO36 interacts specifically with osmotin in solution, (b) binding of radiolabeled osmotin to the plasma membrane, as well as the susceptibility to osmotin, correlate with the abundance of PHO36, and (c) adiponectin and osmotin (proteins whose main chain fold can be overlapped) participate in the same intracellular signaling pathway in C2C12 myocytes via adiponectin receptors (i.e., via mammalian homologues of PHO36).

The evidence that PHO36 and RAS2 function in the same pathway is consistent with a role for PHO36 in nutrition sensing. RAS proteins in yeast are linked to cell division, differentiation, apoptosis, longevity, carbon and nitrogen nutrition (Jazwinski, 1999; Narasirnhan et al., 2001; Forsberg and Ljungdahl, 2001). Adiponectin receptors regulate glucose uptake, fatty acid β-oxidation, and the activities of some proteins that sense the energy status of the cell (Yamauchi et al., 2003a). Recent reports show that adiponectin also induces apoptosis in epithelial cells (Brakenheilm et al., 2004). Because of the link with apoptosis, PHO36 may be connected to the regulation of nutrient acquisition and use in response to cellular energy status or mitochondrial (dys)function. Taken together, these findings indicate a functional similarity between the PHO36 receptor ligand and adiponectin.

The PHO36 osmotin receptor is predicted (based on structural analysis) to comprise seven transmembrane domains, a characteristic feature of the GPCR receptor family. Thaumatin, a sweet-tasting structural homolog of osmotin, binds to sweet taste receptors that are GPCRs (Li et al., 2002). Hence, the ability to bind to GPCRs could be a conserved characteristic of PR-5 proteins that contributes to their specificity for a subset of fungal species targets. The adiponectin receptors, AdipoR2 and AdipoR1 which has significant (29%) sequence homology to PHO36, are also predicted to have the seven transmembrane domains characteristic of GPCRs, activate distinct signaling molecules. However, unlike typical GPCRs, AdipoR1 and AdipoR2 are not coupled with G proteins (Yamauchi et al., 2003 a).

Figure 2:
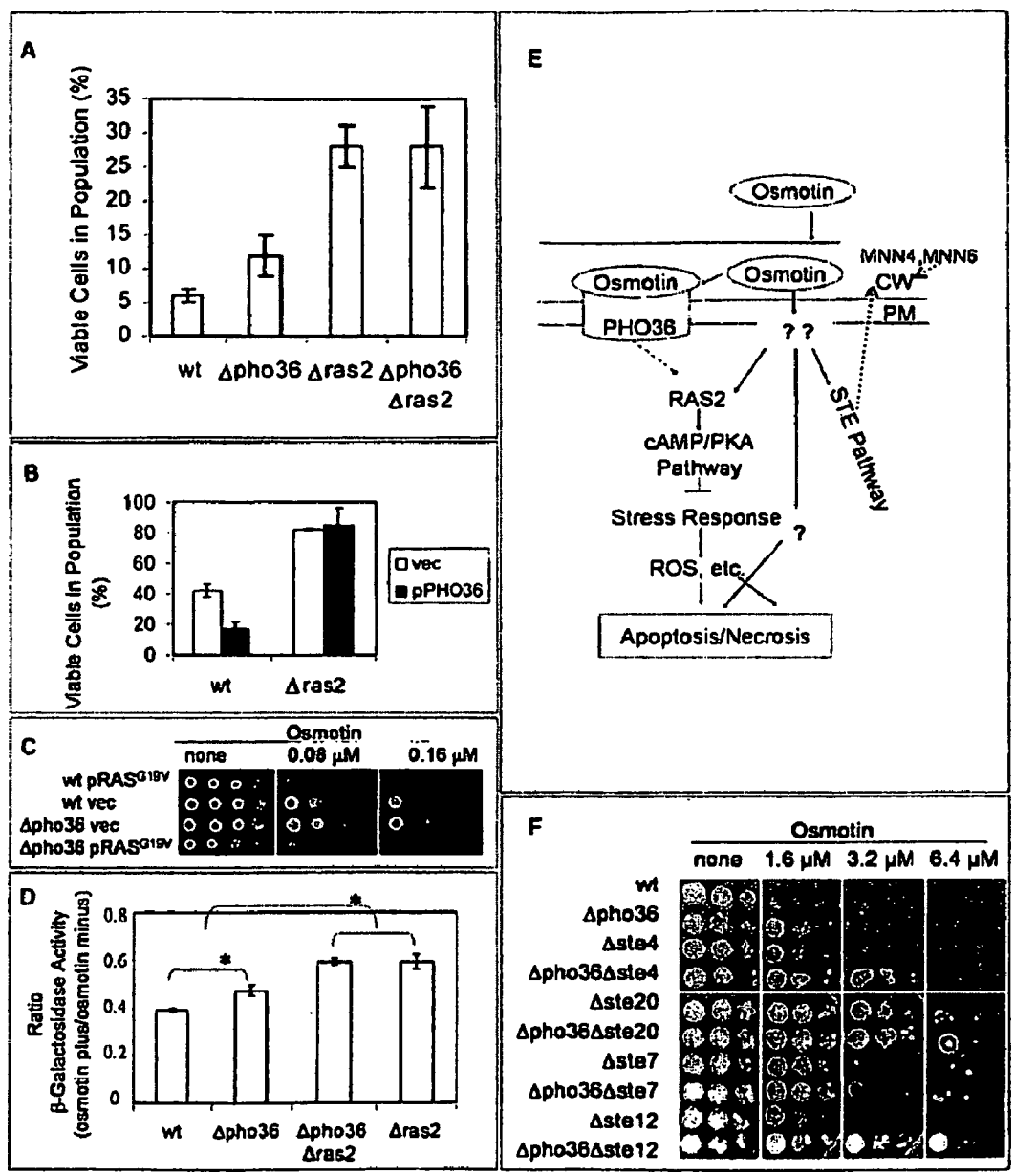
FIG. 2: PHO36 Functions via RAS2 in Osmotin-Induced Apoptosis. A. Cells ($10^8$ ml$^{-1}$) of the wild-type strain (wt), and isogenic Δpho36, Δras2, and Δpho36Δras2 mutant strains were incubated with 5 μM osmotin in YPD at 30° C. under apoptosis-inducing conditions. Cells were washed after 3 hr osmotin treatment and the percent of total cells that were able to survive and form colonies was measured. Values represent the mean of four determinations ±SE. B. Cells ($10^8$ ml$^{-1}$) of the wild type (wt), and Δras2 mutant strains transformed with p426GPD without (vec) or with PHO36 insert (pPHO36) were incubated with 2 μM osmotin in selective SC-glucose medium at 30° C. under apoptosis-inducing conditions. The percent of total cells able to survive and form colonies was measured after 1 hr osmotin treatment as above. Values represent the mean of two determinations ±SE. C. Osmotin sensitivity was assayed by spotting aliquots (2.5 μl) of serial 10-fold dilutions of $A_{600nm}$ 0.4 cultures of strains BWG7a (wt) and the Δpho36 mutant transformed with pAD4M (vec) or pAD4M-RAS2$^{G19V}$ (pRAS$^{G19V}$) on selective SC-glucose medium without (none) or with the indicated osmotin supplements. Plates were photographed after 5 days incubation at room temperature. D. Cells ($10^8$ ml$^{-1}$) of strain BWG7a (wt) and Δpho36, Δpho36Δras2, and Δras2 mutants, transformed with pSTRE-lacZ(LEU2), were treated without (minus) or with (plus) 8 μM osmotin in YPD for 45 min at 30° C. under apoptosis-inducing conditions. Shown are the ratios of β-galactosidase activities measured in cell-free extracts. Each bar represents the mean ±SD (n=3). Statistical comparison of the groups is reported: *p<0.01; no asterisk, no difference. β-galactosidase activities in absence of osmotin were, respectively, respectively, 152±4, 133±3, 705±23, and 139±6 units. The experiment was repeated once with similar results. E. A model for osmotin-mediated cell death pathways is shown: Osmotin activates the RAS2/cAMP pathway and induces suppression of cellular stress responses (STRE-lacZ reporter) followed by accumulation of reactive oxygen species and cell death. Interaction of osmotin with PHO36 activities cell death via RAS2. There may be unidentified upstream components that stimulate the RAS2 cell death pathway in response to osmotin. Pathways controlling stress responses are even more complex, as evidenced by osmotin-independent effects on STRE-lacZ activity in a Δpho36Δras2 genetic background, and are not shown. Symbols: ?, unknown components; ↓, activation; ⊥, inhibition; →, cell wall weakening; CW, cell wall; PM, plasma membrane. F. Aliquots (2.5 μl) of 10-fold serial dilutions of $A_{600\,nm}$ 0.4 cultures of strain BWG7a (wt) and the indicated mutant strains were spotted on YPD agar without (none) or with the indicated osmotin supplements. Plates were photographed after incubation for 2 days at 28° C.
Figure 3:
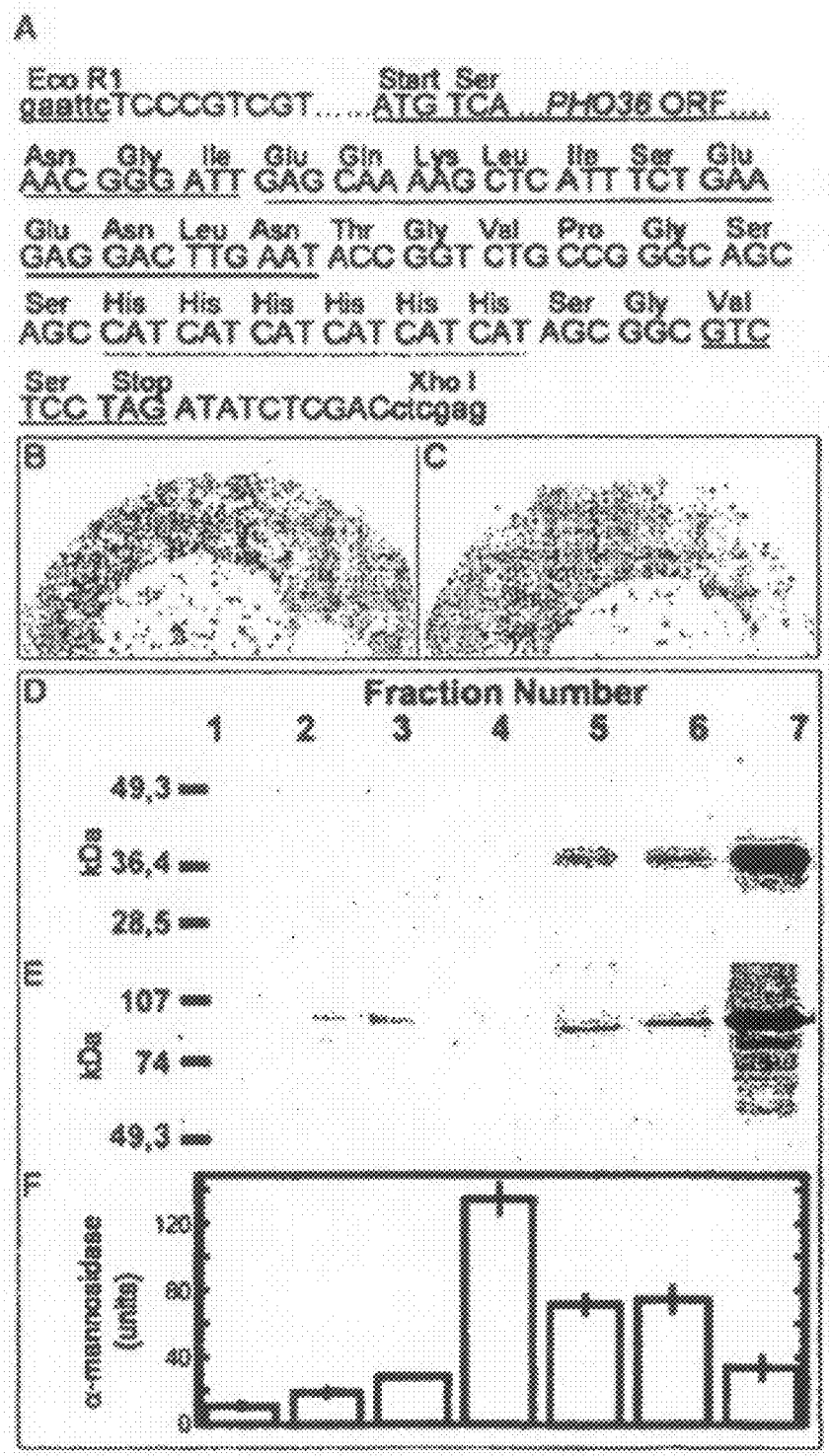
FIG. 3: PHO36 is Localized on the Plasma Membrane. A. The PHO36 MH construct sequence is shown. The EcoR1-XhoI fragment contained 46 nt of the PHO36 gene preceding the start codon, and the natural PHO36 ORF (thin) fused in-frame near its C terminus to a c-myc-tag (thick) and a His tag (dotted underline). B-C. Immunogold localization of tagged PHO36 MH protein. Ultrathin sections of spheroplasts of strain BWG7a carrying the single copy plasmid p416GPD without (B) or with the PHO36 MH insert (pPHO36 MHS[C]) are shown. The 20 nm gold particles, which appear as small black dots, indicate the location of PHO36 MH protein. D-F. Distribution of PHO36 MH protein in cellular membranes. Extracts of cells carrying pPHO36 MHS were fractionated, and distribution of proteins in the membrane-free supernatant fraction (lane 1), total membrane fraction (lane 2), and in sucrose density gradient membrane fractions, from lighter to denser fractions (lanes 3-7, respectively) was analyzed. PHO36 MH (D) and plasma membrane H$^+$-ATPase marker (E) were detected on blots of proteins separated by SDS-PAGE with myc1-9E10 monoclonal antibodies and PMA1 antibodies, respectively. The activity of the vacuolar α-mannosidase marker was measured in these fractions (F) and is given in arbitrary units as increments of $A_{400nm}$ min$^{-1}$ mg$^{-1}$ protein.

There was no evidence for the involvement of the yeast Gα subunits, GPA1 or GPA2, in osmotin-induced cell death. STE4 and STE18 (Gβ and Gγ subunits) are also not coupled to PHO36 (FIG. 2F). Therefore, PHO36 may either not be coupled to heterotrimeric G-proteins like the adiponectin receptors (see Yamauchi et at, 2003a) or may be coupled to the unusual proteins associated with GPA2 (see Harashima and Heitman, 2002). Genetic evidence places PHO36 function upstream of RAS2 in the osmotin-induced apoptotic pathway (FIG. 2), consistent with its plasma membrane location (FIG. 3). Since the effect of PHO36 on osmotin sensitivity is smaller than the effect of RAS2, other "receptors" may also connect to the RAS2 pathway. An alternative function for PHO36 in yeast could be a docking receptor for osmotin that facilitates membrane permeabilization, an activity that has been demonstrated in vitro for PR-5 proteins (Anzlovar et al., 1998; Veronese et al., 2003). This hypothesis is attractive because RAS proteins are not known to be activated by GPCRs in yeast (Rolland et at., 2002), so increased membrane permeabilization has the potential to be the indirect signaling link between RAS2 and PHO36.

The toxic mechanism of action of osmotin is multifactorial, with individual factors making partial contributions to the overall toxicity of the protein (FIG. 2E). Antimicrobial activity of defensive antimicrobial peptides, that are components of innate immunity in all organisms, is also due to a multihit mechanism of action (Hancock and Scott, 2000). Conservation of the multihit mechanism theme of antimicrobial proteins and peptides across species likely reflects host-pathogen co-evolution. It also provides a selective advantage to the host, since the pathogen cannot greatly alter its susceptibility to the host defensive protein/peptide by a single mutation.

Figure 5:
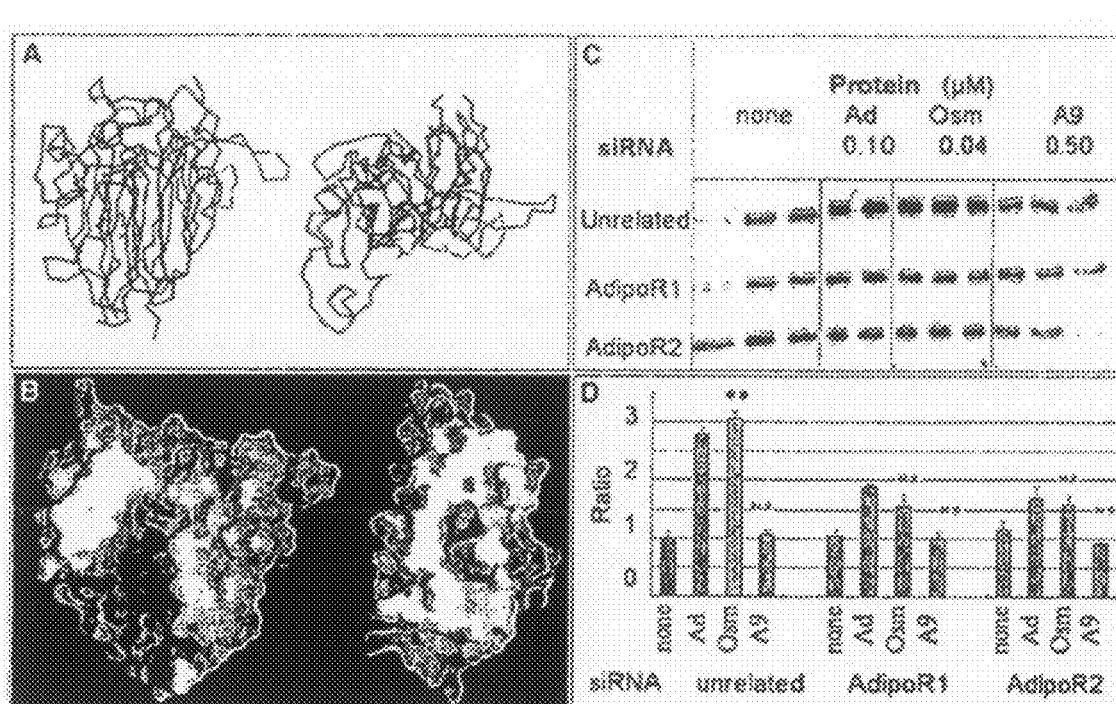
FIG. 5: Comparison of the Structures of Osmotin and Adiponectin. A. Shown are monodiagrams with two different views (90° rotation) of the superposition of the C$^\alpha$ traces of osmotin (yellow-green, blue and magenta) and adiponectin (green). Three domains of osmotin are colored blue (domain I or lectin-like domain), magenta (domain II, amino acids 121-177), and yellow-green (domain III, amino acids 55-82). Three conserved residues which are found in the acidic cleft of osmotin family (Glu84, Asp97, and Asp 102) are drawn in red stick models. B. View of the surface topology of osmotin (left) and adiponectin (right) showing the surface electrostatic potential. The protein surface is colored according to the electrostatic potential from blue (most positive) to white (neutral) to red (most negative). The protein orientations are identical to those shown in (A) (left). The figure was drawn using GRASP (Nicholls et al., 1991). C. Shown are immunoblots of lysates (10 μg protein per lane) of C2C12 myocytes transfected with the indicated siRNAs and treated without (none) or with the indicated concentrations of full-length adiponectin (Ad), osmotin (Osm), and A9 (A9) for 10 min and probed with phosphoAMP kinase-specific antibodies. D. Quantitative analyses of the data in (C). Statistically significant (**) and insignificant (N.S.) difference compared to values with no added protein (none) in the same siRNA set are indicated.

Osmotin and Adiponectin Molecules Exhibit a Similar Overall Fold and Biological Activity. AdipoR1 and AdipoR2, the mammalian homologues of PHO36, are the receptors for adiponectin, a protein hormone secreted by adipocytes. Adiponectin deficiency in mice and humans is associated with insulin resistance and glucose intolerance (Yamauchi et al., 2001a,b; Kubota et al., 2002; Diez and Iglesias, 2003). Increasing adiponectin levels by injection, overexpression or combined weight loss and thiazolidinedione treatment protected mice and humans from obesity and diabetes, reduced insulin resistance (Yamauchi et at., 2001a,b; 2003b) and reduced serum free fatty acids, glucose and triglycerides levels (Fruebis et al., 2001; Diez and Iglesias, 2003). Given the therapeutic potential of adiponectin and the homology between PHO36 and adiponectin receptors, the tertiary structures of osmotin and adiponectin were compared. Adiponectin is a 30 kDa protein with an N-terminal domain that is collagen-like and a C-terminal globular domain that is complement 1q-like (Scherer at al., 1995). The C-terminal globular domain (17 kDa) is often referred to as globular adiponectin and a small amount of globular adiponectin has been reported to be detectable in human plasma. Globular adiponectin has been reported to have potency equivalent to full-length adiponectin for biological activities such as AMP kinase activation, glucose uptake and fatty acid oxidation in myocytes or skeletal muscle (Freubis et al., 2001; Yamauchi et al., 2001a, 2003a, 2003b). Osmotin is a globular protein (26 kDa) that has no significant sequence homology ($\leq 10\%$) with full length or globular adiponectin. X-ray crystallographic studies have shown that globular adiponectin and osmotin comprise antiparallel β strands arranged in the shape of a β barrel (Shapiro and Scherer, 1998; Min et al., 2004). The domain I (the lectin-like β barrel domain) of osmotin can be overlapped with adiponectin with a rmsd of 3.1 Å for 121 Cα atoms, suggesting that two proteins share the lectin-like domain (FIG. 5). Amino acids essential for the sweetness of thaumatin map to a cleft on its surface that corresponds to the acidic cleft formed by Domains I and II of the antifungal PR-5 proteins and is predicted to be important for their antifungal activity (FIG. 5; Kaneko and Kitabatake 2001; Min et al., 2004). This region is localized to the outer surface of the adiponectin trimer, suggesting that it is involved in interaction with the receptor and from our results indicate that it is an important factor controlling binding to the adiponectin receptor(s).

Binding of adiponectin to adiponectin receptors results in activation of AMP kinase by phosphorylation (Yamauchi et al., 2003a). Adiponectin and osmotin are able to induce phosphorylation of AMP kinase in C2C12 myocytes (FIG. 5C, lanes 4-8, row 1), whereas as expected A9, the plant homolog lacking fungicidal activity against yeast, cannot (FIG. 5C, lanes 9-11, row 1). Phosphorylation of AMP kinase requires expression of the adiponectin receptors AdipoR1 and AdipoR2 (FIG. 5C, rows 2 and 3). Thus, the conserved biological function of adiponectin and osmotin in C2C12 myocytes must be due to the common structure in the β barrel domain (domain 1) that is involved in interaction with the adiponectin receptors.

Plant Signal Transduction. Twenty-four loci in *Arabidopsis thaliana* encode ORFs that have thaumatin-family domains (with several of these having putative membrane anchoring sequences and three linked to Ser/Thr kinase domains via a transmembrane domain). At least 2 loci encode sequences that have homology to PHO36. This indicates that thaumatin-like proteins probably have communication roles in plants. C-terminal domains of proteins involved in intercellular communication, immunity and/or energy homeostasis in animals, such as tumor necrosis factor alpha (TNFα), CD40 ligand, and hibernation-regulated proteins have a β barrel fold similar to those of osmotin and adiponectin. The functions of these proteins span the energy homeostasis functions of adiponectin and the apoptosis-inducing and immunity-related functions of osmotin. TNFα and CD40 ligand occur in soluble and type H membrane anchored forms (indicating analogy with predicted *Arabidopsis* thaumatin-like proteins). Unlike osmotin, full length molecules of these proteins have N-terminal "talks" that could be collagenous domains (adiponectin, complement 1q, hibernation-induced proteins) or not (TNFα, CD40 ligand). All of the globular C-terminal adiponectin-like domains form timers. However, osmotin crystallizes as a dimer (Min et al., 2004). It is predominately a monomer in solution, although smaller quantities of higher order structures can be observed in osmotin and thaumatin solutions under certain conditions. Trimerization of the globular adiponectin-like domains, followed by assembly into higher order multimers via N-terminal collagenous domains, is believed to be important for signaling by inducing receptor clustering (Jones et at, 1989; Shapiro and Scherer, 1998; Karpusas et al., 1995; Eck and Sprang, 1989). However, the shared lectin-like β barrel domain of osmotin and adiponectin, the lack of significant homology in other domains, and the high degree of homology between their receptors, when taken together indicate that the conserved lectin-like β barrel domain is a major determinant of receptor binding specificity for these proteins.

Pharmacological significance. Plant proteins of the PR-5 family can act as agonists/antagonists in mammalian adiponectin receptor binding. Osmotin is able to induce adiponectin receptor-mediated AMP kinase phosphorylation in C2C12 myocytes (FIG. 5C). The PR-5 proteins are a large family (24 members in *Arabidopsis thaliana* alone) that is ubiquitous in plants (all species screened have been reported to contain PR-5 proteins). PR-5 proteins are also extremely stable and so would remain active when in contact with human digestive or respiratory systems, as some are known to be allergens (Breiteneder and Ebner, 2000). The functional homology resulting from the similar receptor-binding sites on PR-5 proteins and adiponectin, i.e., a lectin-like β barrel domain, and the high degree of homology between their respective receptors, give pharmacologists access to a very large number of plant products that have actual, or potential, therapeutic uses in mammals, including use in treatment of diabetes, arteriosclerosis, and heart disease or other diseases which are the result of activation or inhibition of adiponectin receptor-mediated metabolic pathways.

Domain II (see FIGS. 5A & 5B) is highly truncated in some thaumatin-like proteins (Genbank Accession Nos. X68197, rice; AF389884, wheat; X97687, wheat). This truncation increases the exposure of the β barrel domain of these proteins, permitting greater overlap with that of adiponectin. Because the structures of these truncated thaumatin-like proteins would thus also be similar to that of adiponectin (in some cases possibly more so than is osmotin), strong adiponectin receptor binding of these proteins is possible.

Osmotin, and related proteins in the PR-5 family having a structurally homologous lectin-like β barrel domain, can be formulated in any of a variety of suitable pharmaceutically acceptable carriers known in the art, and used directly as therapeutic agents to treat a variety of mammalian disorders. Depending on the nature of the interaction with adiponectin receptors (for example having both binding and activating activities, having binding but no activating activity, having no binding activity but having inhibitory activity, etc.), these proteins can be used as agonists or as antagonists of adiponectin activity. Adiponectin is known to mediate a variety of metabolic pathways, the disruption of which can lead to conditions of hyperlipidemia, imbalance in glucose metabolism, insulin resistance, and resulting diseases such as diabetes, arteriosclerosis, obesity, and heart disease. The development of suitable formulations and administration methods for such pharmaceutical compositions (including route of administration and dosing levels) are routine procedures in the pharmaceutical arts.

In addition, osmotin, and related PR-5 proteins having a structurally homologous lectin-like β barrel domain, can be used as surrogates for adiponectin in the development of therapeutic methods for treatment of mammalian disorders in which adiponectin receptor-mediated pathways are implicated. In such methods, the surrogate is used in preliminary testing and development of dosing regimes, administration routes (e.g., injection, oral administration or implantation). The use of abundantly available plant proteins such as osmotin and related proteins can provide a significant cost saving during the research and development phase of such therapeutic methods.

An important, and very powerful, approach to drug development is the "rational design" approach. Rational design of new drugs uses a compound having a known activity that is desired in the new drug as a starting point for the design of what are essentially improved versions of that compound. Through structure/function analysis of the starting compound, the physical properties that contribute to desirable drug qualities (for example, solubility, stability, binding activity or specificity, reduced toxicity and side-effects) can be determined. Once this is done, a structured approach to making modifications to the starting compound can be developed, which more efficiently and predictably leads to the desired improvements. PR-5 proteins having adiponectin agonist or antagonist activity, or both, are valuable tools in such rational drug design.

Conversely, or complementarily, receptors to which osmotin, and related PR-5 proteins having a structurally homologous lectin-like β barrel domain, can specifically bind (for example the yeast receptor PHO36) can be used as screening systems for new therapeutic agents useful in the treatment of mammalian disorders in which adiponectin receptor-mediated pathways are implicated, and in structure/function analysis for rational drug design. Again, the abundant plant sources for these receptors permit the use of high-volume screening methods to rapidly identify and select potential therapeutic agents. Such screening methods can be carried out using a preparation of the isolated receptor (e.g., in solution, or bound for use in a column packing, thin-layer plate, or micro-array), or using a cell line or tissue culture in which the receptor is expressed. In a preferred embodiment, a yeast strain which over-expresses the osmotin receptor PHO36 and is supersensitive to the apoptosis-inducing effects of osmotin, provides an efficient and effective means of performing such screens. Because such a cell line or tissue culture is supersensitive to the affects of osmotin and homologous proteins, screening can be reliably performed using relatively small amounts of the drug candidate compositions. Such a cell line or tissue culture over-expressing PHO36, or a similarly sensitive PR-5 protein receptor, may thus be used as a primary screen to identify chemical and protein/peptide agonists or antagonists of adiponectin receptor function in mammals. Such agonists and/or antagonists are good candidates for therapeutic agents useful for treatment of mammalian conditions in which adiponectin receptor-mediated pathways are implicated, due to the high degree of homology (both structural and functional) between plant PR-5 receptors such as PHO36 and mammalian adiponectin receptors. An ability to bind and affect the plant PR-5 receptor is a strong indication that a compound will possess similar activity with respect to mammalian adiponectin receptors.

Likewise, due to the strict relationship between a protein structure and the nucleic acid sequence that encodes it, DNA and/or RNA sequences encoding osmotin, and related PR-5 proteins having a structurally homologous lectin-like β barrel domain (e.g., [SEQ ID NO. 1 and SEQ ID NO. 2]), can also be used can be used as a means for rational drug design. By identifying features of a coding sequence that relate to desirable properties in the encoded product, modifications can be made directly to the coding sequence in order to make modified and improved drug products that are expressed therefrom. Such structure/function analyses can include comparative analyses using in vitro molecular evolution approaches, such as DNA shuffling, or enhanced selective mutagenesis and phage display or other selective methods for improved peptide function.

EXAMPLE 1

Materials and Methods. The materials and methods used in subsequent Examples 2-6 are as follows.

Strains, Plasmids, and Media. *Escherichia coli* DH5α was used for plasmid propagation and isolation. All the *Saccharomyces cerevisiae* strains were isogenic derivates of the publicly available BWG7a strain described in Becker and Guarante, (1991). Strain BWG7a was obtained by mating type switching with the HO gene (Herskowitz and Jensen, 1991). The Δste, Δras2, and Δmnn6 mutants and procedures for disruption of these loci have been described elsewhere (Yun et al., 1998; Narasimhan et al., 2001). The PHO36 locus was deleted by replacing an internal coding sequence with URA3 (+192 bp to +680 bp relative to the second ATG that is predicted to be the start codon) or kanMX (+72 bp to +740 bp) as described in Wach et al., 1997. The Δydr492 mutation was created by replacing an internal coding sequence (+244 bp to +724 bp) with LEU2, using standard techniques. Precise gene disruptions were confirmed by PCR and Southern blotting. The diploid Δpho361Δpho36 mutant strain was made by crossing the opposite mating type haploid strains, using standard techniques.

For constitutive overexpression, pPHO36 was constructed by isolating the coding region of PHO36 (−46 bp to +957 bp) from strain BWG7a by PCR and cloning into the multicopy plasmid p426GPD (Mumberg et al., 1995). The plasmid pPHO36 MH was constructed from pPHO36 by introducing c-myc and hexa-His tags in-frame at the C-terminus of PHO36 by PCR. Construct PHO36 MH was sequenced to confirm proper fusion of tags. For low level expression of tagged PHO36, the plasmid pPHO36 MHS was made by cloning the PHO36 MH construct in the single copy plasmid p416GPD using appropriate restriction enzyme sites. The plasmid pNC267 containing STE7-Myc translational fusion has been described (Zhou et al., 1993). RAS2$^{G19V}$ was cloned in pAD4M using standard techniques.

To construct STRE-lacZ (LEU2), the chimeric STRE-lacZ gene from pSTRE-lacZ(TRP) (Stanhill et al., 1999) was isolated by PCR using 5'-CCCMGCTTCAGTTATTACCCTC-GAC-3' as forward primer and 5'-CCCGGGTTATTTTTGA-CACCAGACCAA-3' as reverse primer. The insert was subcloned into pGEM-T easy, and sequenced, excised with Apall and Xmal, and subcloned into the corresponding sites of pRS315.

Standard procedures were used for yeast media preparation and genetic analyses (Becker and Guarante, 1991; Sherman, 1991). Yeast transformations were performed by the lithium acetate method described in Elble, 1992. Analysis of yeast strain phenotype was performed according to standard procedures (Hampsey, 1997).

cDNA Library and Cloning. Strain BWG7a was transformed with a GALL-regulated yeast cDNA expression library using the methods described in Liu et al. (1992). Approximately 50,000 primary transformants selected on SC-glucose medium were replica plated sequentially onto 0.003% methylene blue containing selective SC-galactose medium without or with osmotin (0.2 µM), a sublethal concentration under these conditions. Transformants that turned blue or failed to grow in presence of osmotin were then selected. The galactose-dependent osmotin supersensitive phenotype of these transformants was confirmed by spot assays on selective SC-galactose and SC-glucose media with a range of osmotin supplements. Plasmids carried by these transformants were isolated using the methods described in Robzyk and Kassir (1992), and their cDNA inserts were sequenced using standard techniques.

Purification of Total Membranes and Subcellular Fractionation. Total membrane fraction was isolated from 1 liter cultures ($A_{600nm}$ 1.0) of yeast cells expressing PHO36 MH from the single copy plasmid pPHO36 MHS as described in David et al. (1997). It was resuspended in 3 ml of 10% (w/w) sucrose in buffer A (50 mM HEPES, pH 7.5/5 mM EDTA/2 µg.ml$^{+1}$ aprotinin/2 µg.ml$^{-1}$ chymostatin/2 µg.ml$^{-1}$ pepstatin/1 µg.ml$^{-1}$ leupeptin/2 mM benzamidine/1 mM PMSF) and layered on top of a 5-step sucrose gradient (15, 28, 35, 43 and 53% w/w) in buffer A (2 ml per step). After centrifugation for 12 hr at 20,000 rpm in a Beckman SW40 rotor at 4° C., fractions (2 ml) were collected from top to bottom. They were diluted with three volumes of water and centrifuged at 186,000×g for 30 min. The pellets were resuspended in 200 µl of buffer (10 mM Mes.KOH [pH 6.5], 10% glycerol, protease inhibitors as in buffer A)

Protein Methods and Enzyme Assays. Osmotin purification and assays of osmotin cytotoxicity were performed as described previously in Yun et al. (1997), Ibeas et al. (2000), and Narasimhan et al. (2001). Alpha-mannosidase activity was measured using p-nitrophenyl-a-D-mannopyranoside (Sigma) as substrate. Protein concentration was determined with the Bio-Rad protein assay kit (Bio-Rad). Protein extracts were fractionated by SDS-PAGE on 10% polyacrylamide gels and transferred to nitrocellulose membranes. PHO36 MH and the plasma membrane H$^+$-ATPase were detected on immunoblots of the separated proteins by the ECL method (Amersham Biosciences). Myc1-9E10 monoclonal antibodies (2 µg.ml$^{-1}$; CalBiochem) and rabbit PMA1 polyclonal antibodies (1:10000 dilution) (Monk et al., 1991) were used as primary antibodies and horseradish peroxidase-conjugated anti-mouse or anti-rabbit immunoglobulin G (1:5000 dilution; Promega) were used as secondary antibodies.

β-Galactosidase assay method, cell growth conditions, osmotin treatments, and preparation of cell extracts for this purpose have been described earlier (Narasimhan et al., 2001). β-Galactosidase activities were expressed in arbitrary units as increments of $A_{400nm}$ min$^{-1}$ mg$^{-1}$ protein. The protocols for purifying recombinant murine adiponectin and measuring activation of AMP kinase in murine C2C12 myocytes were as described in Yamauchi, et al. (2003a).

Immunogold localization. Yeast spheroplasts were fixed and embedded as described in Yun et al. (1997), except that IM sorbitol was added to the fixative solution as osmotic stabilizer and the sodium metaperiodate treatment was omitted. Ultrathin sections were reacted successively with myc1-9E10 monoclonal antibodies (5 µg.ml$^{-1}$) and goat anti-mouse IgG conjugated to 20 nm gold particles (1:50 dilution; Ted Pella, Inc., Redding, Calif.). Sections were viewed with a transmission electron microscope EM200 (Philips Electronic Instruments Co., Mahwah, N.J.).

$^{35}$S-Osmotin Binding Assay. Osmotin was radiolabeled to a specific-activity of 12 Ci mmol$^{-1}$ using the $^{35}$SLR reagent (Amersham), according to manufacturer's instructions. Yeast cells were grown YPD medium until A600 nm 0.6 and then harvested by centrifugation. The pellet was resuspended in 1 M sorbitol (A$_{600\,nm}$ 6) and treated with lyticase (100 U ml$^{-1}$). After digestion of the cell wall was completed, spheroplasts were collected by centrifugation, washed twice with 1 M sorbitol and resuspended in 1 M sorbitol ($10^9$ ml$^{-1}$). The binding reaction was initiated by the addition of 2 µl of $^{35}$S-osmotin (1 µCi, 3 µg) to 300 µl of spheroplasts ($0.3 \times 10^9$). After 60 min incubation at 30° C., triplicate aliquots (50 µl) of the reaction mixture were diluted into ice-cold 1 M sorbitol (1.5 ml). Spheroplasts were collected by centrifugation, washed twice, resuspended 1 M sorbitol (50 µl) and counted in a liquid scintillation counter in 5 ml of ECOLUME (ICN Biomedicals). For competition experiments, spheroplasts were preincubated for 30 min with A9, osmotin or BSA before adding $^{35}$S-osmotin.

Protein interaction assays in solution. Osmotin was coupled to CNBr-activated Sepharose 4B (Pharmacia Biotech) according to the manufacturer's instructions. Total membrane fraction (from 50 ml culture) was isolated as described above, and resuspended in 200 µl of buffer (1% n-dodecyl-β-D-maltoside, 10% glycerol, 50 mM Tris.HCl [pH 7.6], 100 mM NaCl, 1 mM PMSF). Total membrane fraction (50 µl) was incubated with osmotin-Sepharose 4B (200 µl) in 50 mM Tris.HCl [pH 7.6], 1 mM PMSF (1 ml) in the absence or presence of competitor protein (100 µg) with gentle agitation for 4 hr at room temperature. After 5 washes with 50 mM Tris.HCl [pH 7.6], 0.1% Triton X-100, the complexes were dissociated by incubating in sample buffer (1% SDS, 50 mM Tris.HCl [pH 7.6], 10% glycerol) for 30 min at room temperature and separated by 10% SDS-PAGE. PHO36 MH protein was immunodetected on blots using myc1-9E10 monoclonal antibodies.

EXAMPLE 2

PHO36 mediates sensitivity to osmotin. Genes that conferred an osmotin supersensitive phenotype to the yeast strain BWG7a were isolated using a GAL1-regulated cDNA expression library (Liu et al., 1992). From about 50,000 primary transformants selected in SC-glucose medium, a total of 12 transformants that consistently exhibited hypersensitivity to osmotin in SC-galactose medium but displayed normal sensitivity to osmotin in glucose media were selected as putative osmotin supersensitive clones. Plasmids carried by these transformants were isolated, reintroduced into BWG7a to confirm that they were able to confer galactose-dependent osmotin-supersensitive phenotype, and their cDNA inserts were sequenced. The ORE20 gene (for osmotin resistance), corresponding to locus YOL002c/PHO36 (Karpichev et al., 2002), was selected for further study. This gene was found to encode protein of 317 amino acids (36.3 kDa) that is predicted to contain seven membrane-spanning domains (Saccharomyces Genome Database), a characteristic feature of GPCRs.

The cDNA originally isolated from the screening (PHO36t) was truncated, missing the first 19 nucleotides downstream of its hypothetical start codon. Cells of strain BWG7a overexpressing PHO36t from the GAL1 promoter were more sensitive to osmotin than control cells transformed with the empty vector, and failed to form colonies in osmotin-containing media (FIG. 1A). Growth inhibition resulted from increased susceptibility to osmotin-induced cell death as demonstrated by measuring viable counts after one hour of osmotin treatment. In galactose medium, the IC$_{50}$ for osmotin of cells overexpressing PHO36t was 3-fold lower than that of control cells transformed with the empty vector (0.2 µM and 0.6 µM, respectively). The same phenotype, in glucose medium, was observed for cells overexpressing the full-length PHO36 from the constitutive GPD promoter in a multicopy plasmid. Conversely, disruption of PHO36 increased osmotin resistance (FIG. 2F), which was estimated as a 3-fold increase in IC$_{50}$ for osmotin when compared to the wild type strain (1.6 µM and 0.6 µM, respectively).

Overexpression of PHO36 in strain BWG7a increased osmotin sensitivity of spheroplasts (FIG. 1B, inset). Conversely, spheroplasts of the Δpho36 mutant were more resistant to osmotin than spheroplasts of the wild-type strain (FIG. 1B). These results show that PHO36 mediates sensitivity to osmotin at the level of the plasma membrane, unlike previously identified cell wall-mediated osmotin resistance determinants (Yun et al., 1997; Ibeas et al., 2000, 2001).

EXAMPLE 3

Phenotype related to the expression level of PHO36. A Δpho36 mutant (Δyo1002c) in *S. cerevisiae* strain W3031A has been reported to grow poorly on myristate and non-fermentable carbon sources (Karpichev et al., 2002). However, growth of isogenic wild-type strain BWG7a, pho36, and PHO36-overexpressing cells was indistinguishable when colony formation or cell growth rate was measured with different carbon sources (2% glucose, 2% galactose, 2% ethanol, 2% lactic acid, 2% potassium acetate, 3% glycerol, or 3% glycerol and 0.1% oleic acid), nitrogen sources (none, urea, asparagine or proline), temperatures (16, 28 and 37° C.), and pH (3, 6.6 and 8).

No differences were found in the sensitivity of wild-type, Δpho36, and PHO36-overexpressing cells to osmotic or ionic stresses as measured by sorbitol (2M), NaCl, KCl, or NH$_4$Cl (0.75 and 1.5M) treatments. PHO36 was not required for invasive growth since deletion of PHO36 in the Σ1278 strain (Gimeno et al., 1992) did not abolish its ability to penetrate agar. The percentage of sporulation determined for diploid PHO36/PHO36 cells (21.33±5.89) and diploid Δpho36/Δpho36 cells (26.33±3.36) were not significantly different. Subtle differences that were found included difference in mating efficiency (Δpho36, 6.9%; wild-type, 2.7%), sensitivity to heat-shock (46±10% survival after 20 min. at 50° C. for Δpho36 cells, compared to 78.3±3.38% for wild-type cells), and resistance to the cell wall perturbing agents calcofluor white and hygromycin B (Δpho36 cells were more resistant). Δpho36 cells were previously shown to be more resistant than wild type cells to the cell membrane perturbing antibiotic nystatin (Karpichev et al., 2002).

EXAMPLE 4

PHO36 functions in the RAS2 signaling pathway activated by osmotin to induce cell death. Osmotin suppresses cellular stress signaling via the RAS2/cAMP pathway to promote programmed cell death (Narasimhan et al., 2001). Thus, osmotin resistance is increased by null mutation of RAS2 and decreased by expression of the dominant active RAS2$^{G19V}$ allele in the wild type strain (Narasimhan et al., 2001). Mutation of PHO36 in a Δras2 mutant did not increase osmotin resistance of the Δras2 mutant under apoptosis-inducing conditions (Narasimhan et al., 2001), suggesting that PHO36 functions in the RAS2-mediated osmotin-induced apoptotic pathway (FIG. 2A). Overexpression of PHO36 from a multicopy plasmid in the Δras2 mutant did not significantly increase osmotin sensitivity, whereas overexpression of PHO36 in the wild type strain rendered it more sensitive to osmotin (FIG. 2B). Also, as expected if PHO36 functions in the cell death pathway upstream of RAS2, expression of the dominant active RAS2$^{G19v}$ allele in the Δpho36 mutant increased sensitivity to osmotin (FIG. 2C).

STRE (stress responsive) promoter elements fused to a lacZ reporter gene have been shown to respond to RAS2/cAMP pathway-dependent stress signaling (Stanhill et al., 1999). The chimeric STRE-lacZ construct has also been used to demonstrate that osmotin suppresses cellular stress signaling via the RAS2/cAMP pathway to promote cell death (Narasimhan et al., 2001) and was used here to examine the role of PHO36 in osmotin-induced cellular signaling (FIG. 2D). Consistent with the earlier report that extent of cell death in a population of osmotin-treated yeast cells is proportional to suppression of STRE-lacZ reporter gene activity (Narasimhan et al., 2001), suppression of β-galactosidase activity was greatest in wild-type cells, lower in the Δpho36 mutant and least in the Δras2 and the Δpho36Δras2 double mutants (FIGS. 2A and 2D). These results indicate that PHO36 functions in the cell death signaling pathway upstream of RAS2. It should be noted that in the absence of osmotin treatment, STRE-lacZ activity in the Δpho36Δras2 double mutant was lower than that in the Δras2 mutant (FIG. 2D, legend), indicating that there are RAS2-independent osmotin-independent pathways controlling stress responses that become evident only in the absence of PHO36.

These and earlier data (Yun et al., 1998; Ibeas et al., 2000; Narasimhan et al., 2001) are consistent with the occurrence of pathways controlling osmotin toxicity (FIG. 2E). For example, the partial osmotin resistance of the Δpho36 mutant relative to that of the Δras2 mutant could be explained by functional redundancy of PHO36 with other protein(s). The hypothetical protein encoded by the YDR492w locus shares the greatest identity (44%) with PHO36. Therefore, the osmotin sensitivities of strains bearing Δydr492 and Δpho36Δydr492 mutations were tested but were found to be indistinguishable from those of the wild type and Δpho36 strains, respectively.

Previous genetic studies have revealed that osmotin also subverts a signal transduction pathway in yeast to weaken defensive cell wall barriers and increase its cytotoxic efficacy (Yun et al., 1998). Components of the pathway include the β (STE4) and γ (STE 18) subunits of a heterotrimeric G-protein, the protein kinase STE20, the MAP kinase module consisting of STE5, STE11, STE7, FUS3, KSS1, and the transcription factor STE12 and are also shared by the pheromone response and invasive growth signaling pathways. However, the G-protein coupled pheromone receptors STE2 and STE3 were dispensable for osmotin-induced signal transduction. Since PHO36 has the structural features of a G-protein coupled receptor, but mediates osmotin sensitivity, the possibility that PHO36 might act as the receptor linked to the MAP kinase pathway that is activated by osmotin was tested. Simultaneous disruption of PHO36 in Δste18, Δste20, Δste7, and Δste12 mutants resulted in a greater osmotin resistance than disruption of either gene alone (FIG. 2F) indicating that STE genes and PHO36 function in different processes leading to osmotin sensitivity. This is consistent with results that place PHO36 in the RAS2 signaling pathway since previous observations showed that RAS2 and the STE genes function in genetically distinct pathways leading to osmotin sensitivity (Narasimhan et al., 2001).

Full sensitivity to osmotin requires the presence of mannosylphosphate residues on cell wall glycoproteins (Ibeas et al., 2000). Addition of mannosylphosphate is dependent on the mannosylphosphate transferase MNN6. Mutation of PHO36 increased osmotin resistance of a Amnn6 mutant and overexpression of PHO36 increased osmotin sensitivity of the Amnn6 mutant as expected if they functioned in different processes regulating osmotin resistance.

These data collectively and consistently show that PHO36 functions upstream of RAS2 in the programmed cell death signaling pathway activated by osmotin.

EXAMPLE 5

PHO36 is a plasma membrane protein. PHO36 has the structural features of GPCRs. Typically these proteins are integral plasma membrane proteins. The subcellular localization of PHO36 was therefore determined using an immunocytochemical procedure for electron microscopy. For this purpose, a recombinant PHO36 MH protein, in which a c-myc epitope and a hexa-His tag were fused in-frame at the C-terminal of PHO36, was expressed in BWG7a cells from the constitutive GPD promoter (FIG. 3A). Overexpression of PHO36 MH from a multicopy plasmid increased osmotin sensitivity, indicating that PHO36 MH was functional. PHO36 MH was detected with myc1-9E10 monoclonal antibodies on ultrathin sections of spheroplasts generated from cells expressing low levels of PHO36 MH from the single copy plasmid pPHO36 MHS. Gold particle labeling indicated a plasma membrane localization of PHO36 MH (FIGS. 3B and 3C). Accordingly, PHO36 MH was immunodetected in the denser fractions of total membranes fractionated on a sucrose gradient (FIG. 3D), and co-fractioned with plasma membrane H$^+$-ATPase (FIG. 3E), but not with vacuolar α-mannosidase (FIG. 3F).

EXAMPLE 6

Figure 4:
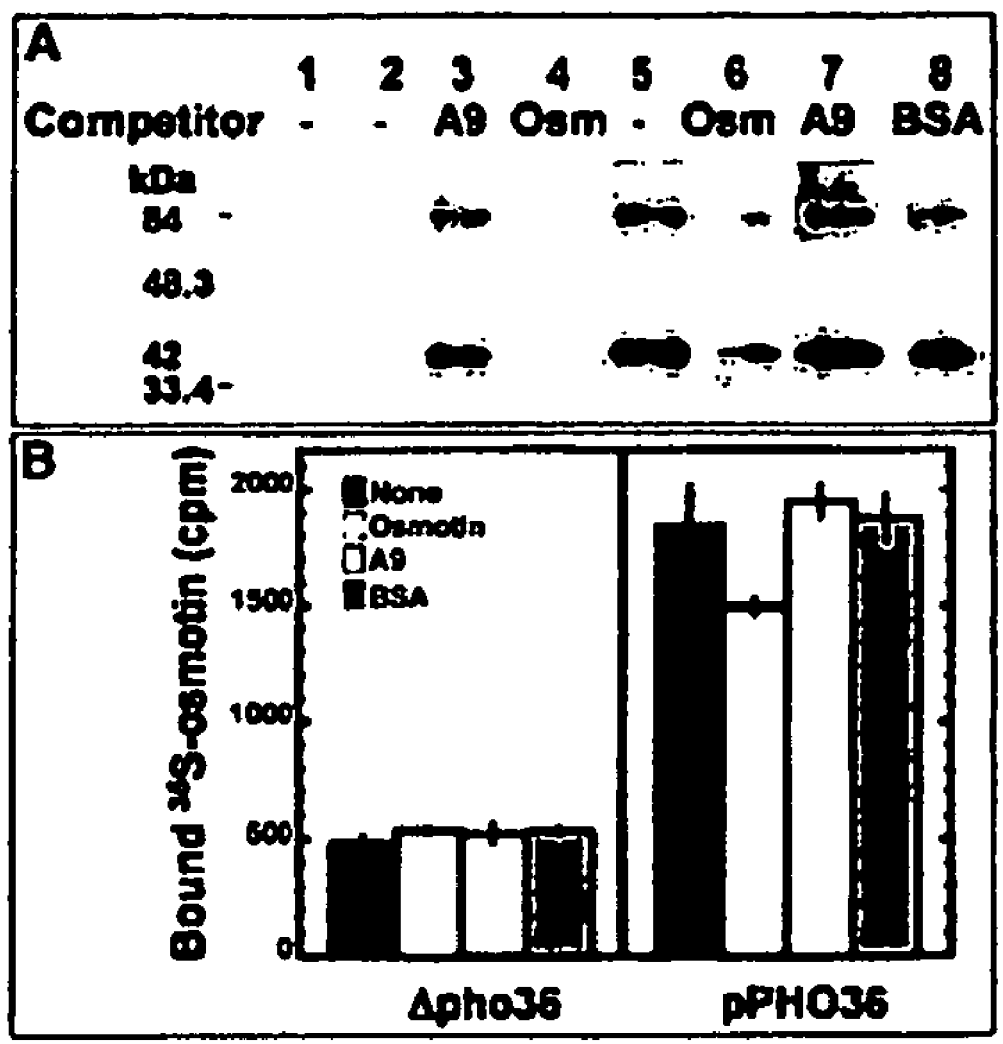
FIG. 4: PHO36 Interacts Specifically with Osmotin In Vitro and In Vivo. A. Osmotin-Sepharose 4B was incubated with cell extract of the strain BWG7a expressing the fusion protein STE7-Myc (lane 1), total membrane fraction purified from the strain ΔPHO36 (lane 2) or total membrane fraction purified from the strain BWG7a expressing c-myc tagged PHO36 from the plasmid pPHO36 MH (lanes 3-8) in the absence (lanes 1, 2, and 5) or presence of the competitor proteins A9 (100 μg, lane 3; or 10 μg, lane 7), osmotin (Osm; 100 μg, lane 4; or 10 μg, lane 6), or BSA (100 μg, lane 8). After extensive washing, bound proteins were dissociated, separated by SDS-PAGE and the c-Myc tag was immunodetected with myc1-9E10 antibodies. B. Spheroplasts ($10^9$ ml$^{-1}$) derived from the Δpho36 mutant (Δpho36), and the wild-type strain BWG7a carrying the plasmid pPHO36 MH (pPHO36) were incubated with $^{35}$S-osmotin (0.4 μM, 0.16 μCi) for 1 hr, without (none) or with a 10-fold molar excess of A9, BSA, or osmotin as competitors. After extensive washing, $^{35}$S-osmotin retained on spheroplasts was counted.

PHO36 binds specifically to active PR-5 isoforms. Membrane fractions purified from cell lysates of the PHO36 MH-overexpressing strain and the Δpho36 mutant were incubated with osmotin-Sepharose-4B. After extensive washing, bound proteins were dissociated, separated by SDS-PAGE and PHO36 MH was immunodetected with myc1-9E10 monoclonal antibodies. Two bands representing PHO36 MH monomers and dimers, with apparent molecular mass about 36 and 72 kDa respectively, were detected in membrane fractions of the PHO36 MH-overexpressing strain (FIG. 4A, lanes 3-8) but were absent in membrane fractions of the Δpho36 mutant (FIG. 4A, lane 2). No bands were detected in cell extracts of a yeast strain expressing c-myc tagged STE7, indicating that binding of recombinant PHO36 MH to osmotin was specific for PHO36 and not the c-myc tag (FIG. 4A, lane 1). Inclusion of free osmotin in the binding reaction reduced binding whereas inclusion of A9 or BSA had no effect (FIG. 4A, lanes 3-8), demonstrating the specificity of the osmotin-PHO36 interaction. A9, purified from the plant *Atripler nummularia*, is a PR-5 protein that is less active against yeast cells and spheroplasts than osmotin but is active against other fungal species (Yun et at., 1997), and was therefore used as a control for binding selectivity.

Spheroplasts of the strain overexpressing PHO36 MH, the Δpho36 mutant (FIG. 4B) and the wild-type strain transformed with empty vector all bound $^{35}$S-osmotin in vivo. The amount of $^{35}$S-osmotin that was bound to spheroplasts of the Δpho36 mutant and could not be displaced by inclusion of a 10-fold excess of cold osmotin during the incubation represents the extent of non-specific binding (FIG. 4B, left). After subtracting this non-specific binding, it was estimated that $^{35}$S-osmotin binding to spheroplasts of the PHO36 MH-overexpressing strain was linear for 60 min without loss of spheroplast viability. Spheroplasts of the PHO36 MH-overexpressing strain bound approximately 3 times more $^{35}$S-osmotin than spheroplasts of the wild-type strain transformed with empty vector. The binding of $^{35}$S-osmotin to spheroplasts of the strain overexpressing PHO36 MH (FIG. 4B, right) was partially out-competed by inclusion of a 10-fold excess of cold osmotin in the reaction, but was not out-competed either by A9, the osmotin homologue that is inactive in yeast, or BSA. Thus PHO36, the plasma membrane protein required for maximal sensitivity to osmotin, is also involved in the specific binding of osmotin to the yeast spheroplasts that precedes cell death.

DOCUMENTS CITED

The following documents are incorporated by reference to the extent they enable the present invention:

Anzlovar, S., Serra, M. D., Dermastia, M., and Menestrina, G. (1998). Membrane permeabilizing activity of pathogenesis-related protein linusitin from flax seed. Mol. Plant-Microbe Interact. 11, 610-617.

Becker, D. M., and Guarente, L. (1991). High-efficiency transformation of yeast by electroporation. In Methods Enzymol., C. Guthrie and G. R. Fink, eds. (New York: Academic Press) 194, 182-187.

Brakenhielm, E., Vietonmaki, N., Cao, R., Kihara, S., Matsuzawa, Y., Zhivotovsky, B., Funahashi, T. and Cao, Y. (2004). Adiponectin-induced antiangiogenesis and antitumor activity involve caspase-mediated endothelial cell apoptosis. Proc. Natl. Acad. Sci. USA. 101, 2476-2481.

Breiteneder, H., and Ebner, C. (2000). Molecular and biochemical classification of plant-derived food allergens. J. Allergy Clin. Immunol. 106, 27-36.

David, N. E., Gee, M., Andersen, B., Naider, F., Thomer, J., and Stevens, R. C. (1997). Expression and purification of the Saccharomyces cerevisiae alpha-factor receptor (Step 2p), a 7-transmembrane-segment G protein-coupled receptor. J. Biol. Chem. 272, 15553-15561.

Diez, J. J., and Iglesias, P. (2003). The role of the novel adipocyte-derived hormone adiponectin in human disease. Eur. J. Endocrinol. 148, 293-300.

Ding, S. T., Liu, B. H. and Ko, Y. H. (2004). Cloning and expression of porcine adiponectin and adiponectin receptor 1 and 2 genes in pigs, J. Anim. Sci. 82 (11), 3162-3174.

Eck, M. E. and Sprang, S. R. (1989). The structure of tumor necrosis factor-a at 2.6° A resolution. J. Biol. Chem. 264, 17595-17605.

Elble, R. (1992). A simple and efficient procedure for transformation of yeasts. Biotechniques 13, 18-20.

Forsberg, H., and Ljungdahl, P. O. (2001). Sensors of extracellular nutrients in Saccharomyces cerevisiae. Curr. Genet. 40, 91-109.

Fruebis, J., Tsao, T. S., Javorschi, S., Ebbets-Reed, D., Erickson, M. R., Yen, F. T., Bihain, B. E. and Lodish, H. F. (2001). Proteolytic cleavage product of 30-kDa adipocyte complement-related protein increases fatty acid oxidation in muscle and causes weight lodd in mice. Proc. Natl. Acad. Sci. USA. 98, 2005-2010.

Gimeno, C. J., Ljungdahl, P. O., Styles, C. A., and Fink, G. R. (1992) Unipolar cell divisions in the yeast Saccharomyces cerevisiae lead to filamentous growth: regulation by starvation and RAS. Cell 68, 1077-1090.

Hampsey, M. (1997). A review of phenotypes in Saccharomyces cerevisiae. Yeast 13, 1099-1133.

Hancock, R. E, and Scott, M. G. (2000). The role of antimicrobial peptides in animal defenses. Proc. Natl. Acad. Sci. USA. 97:8856-8861.

Harashima, T., and Heitman, J. (2002). The Galpha protein Gpa2 controls yeast differentiation by interacting with kelch repeat proteins that mimic Gbeta subunits. Mol. Cell. 10, 163-173.

Herskowitz, I., and Jensen, R. E. (1991). Putting the HO gene to work: Practical uses for mating-type switching. In Methods Enzymol., C. Guthrie and G. R. Fink, eds. (New York: Academic Press) 194, 132-145.

Ibeas, J. I., Lee, H., Damsz, B., Prasad, D. T., Pardo, J. M., Hasegawa, P. M., Bressan, R. A., and Narasimhan, M. L. (2000). Fungal cell wall phosphomannans facilitate the toxic activity of a plant PR-5 protein. Plant J. 23, 375-383.

Ibeas, J. I., Yun, D.-J., Damsz, B., Narasimhan, M. L., Uesono, Y., Ribas, J. C., Lee, H., Hasegawa, P. M., Bressan, R. A., and Pardo, J. M. (2001). Resistance to the plant PR-5 protein osmotin in the model fungus Saccharomyces cerevisiae is mediated by the regulatory effects of SSD1 on cell wall composition. Plant J. 25, 271-280.

Jazwinski, S. M. (1999). The RAS genes: a homeostatic device in Saccharomyces cerevisiae longevity. Neurobiol. Aging 20, 471-478.

Jones, E. Y., Stuart, D. I., and Walker, N. P. (1989). Structure of tumour necrosis factor. Nature. 338, 225-228.

Kaneko, R., and Kitabatake, N. (2001). Structure-sweetness relationship in thaumatin: importance of lysine residues. Chem Senses 26, 167-177.

Karpichev, I. V., Cornivelli, L. and Small, G. M. (2002). Multiple regulatory roles of a novel Saccharomyces cerevisiae protein, encoded by YOL002c, in lipid and phosphate metabolism. J. Biol. Chem. 277, 19609-19617.

Karpusas, M., Hsu, Y. M., Wang, J. H., Thompson, J., Lederman, S., Chess, L., and Thomas, D. (1995). A crystal structure of an extracellular fragment of human CD40 ligand. Structure. 3, 1031-1039.

Kubota, N., Terauchi, Y., Yamauchi, T., Kubota, T., Moroi, M., Matsui, J., Eto, K., Yamashita, T., Kamon, J., Satoh, H., Yano, W., Froguel, P., Nagai, R., Kimura, S., Kadowaki, T., and Noda, T. (2002). Disruption of adiponectin causes insulin resistance and neointimal formation. J. Biol. Chem. 277, 25863-25866.

Li, X., Staszewski, L., Xu, H., Durick, K., Zoller, M. & Adler, E. (2002). Human receptors for sweet and umami taste. Proc: Natl. Acad. Sci. USA 99, 4692-4696.

Liu, H., Krizek, J. & Bretscher, A. (1992). Construction of a GALL-regulated yeast cDNA expression library and its application to the identification of genes whose overexpression causes lethality in yeast. Genetics 132, 665-673.

Lyons, T. J., VIIIa, N.Y., Regalia, L. M., Kupchak, B. R., Vagstad, A., and Eide, D. J. (2204). Metalloregulation of yeast membrane steroid receptor homologs. Proc. Natl. Acad. Sci. USA 101, 5506-5511.

Min, K., Ha, S. C., Hasegawa, P. M., Bressan, R. A., Yun, D. J. and Kim, K. K. (2004). Crystal structure of osmotin, a plant antifungal protein. Proteins 54, 170-174.

Monk, B. C., Montesinos, C., Ferguson, C., Leonard, K., and Serrano, R. (1991). Immunological approaches to the transmembrane topology and conformational changes of the carboxyl-terminal regulatory domain of yeast plasma membrane H(+)-ATPase. J. Biol. Chem. 266, 18097-18103.

Mumberg, D., Muller, R., and Funk, M. (1995). Yeast vectors for the controlled expression of heterologous proteins in different genetic backgrounds. Gene 156, 119-122.

Narasimhan, M. L., Damsz, B., Coca, M. A., Ibeas, J. I., Yun, D.-J., Pardo, J. M., Hasegawa, P. M., and Bressan, R. A. (2001). A plant defense protein induces microbial apoptosis. Mol. Cell. 8, 921-930.

Narasimhan, M. L., Lee, H., Damsz, B., Singh, N. K., Ibeas, J. L., Matsumoto, T. K., Woloshuk, C. P. and Bressan, R. A. (2003). Overexpression of a cell wall glycoprotein in *Fusarium oxysporum* increases virulence and resistance to a plant PR-5 protein. Plant J. 36: 390-400.

Nicholls, A., Sharp, K. A. and Honig, B. (1991) Protein folding and association: insights from the interfacial and thermodynamic properties of hydrocarbons. Proteins 11: 281-296.

Robzyk, K., and Kassir, Y. (1992). A simple and highly efficient procedure for rescuing autonomous plasmids from yeast. Nucleic Acids Res. 20, 3790.

Rolland, F., Winderickx, J. and Thevelein, J. M. (2002). Glucose-sensing and signaling mechanisms in yeast. FEMS Yeast Res. 2, 183-201.

Scherer, P. E., Williams, S., Fogliano, M., Baldini, G., and Lodish, H. F. (1995). A novel serum protein similar to C1 q, produced exclusively in adipocytes. J. Biol. Chem. 270, 26746-26749.

Shapiro L, Scherer P E. (1998). The crystal structure of a complement-1q family protein suggests an evolutionary link to tumor necrosis factor. Curr. Biol. 8:335-338.

Sherman, F. (1991). Getting started with yeast. In Methods in Enzymology, eds. Guthrie, C. & Fink, G. R. (Academic Press, New York), 194, 3-21.

Stanhill, A., Schick, N., and Egelberg, D. (1999). The yeast Ras/cyclic AMP pathway induces invasive growth by suppressing the cellular stress response. Mol. Cell. Biol. 19, 7529-7538.

Veronese, P., Ruiz M., Coca, M. A., Hernandez-Lopez, A., Lee, H., Ibeas, J. I., Damsz, B., Pardo, J. M., Hasegawa, P. M., Bressan, R. A., & Narasimhan, M. L. (2003) In defense against pathogens. Both plant sentinels and foot soldiers need to know the enemy. Plant Physiol. 131, 1580-1590.

Wach, A., Brachat, A., Alberti-Segui, C., Rebischung, C., and Philippsen, P. (1997). Heterologous HIS3 marker and GFP reporter modules for PCR-targeting in *Saccharomyces cerevisiae*. Yeast, 13, 1065-1075.

Weickmann, J. L., Blair, L. C., and Wilcox, G. L. (1994) High level expression of thaumatin in *Saccharomyces cerevisiae*. In Thaumatin, M. Witty and J. D. Higginbotham, eds. (Boca Raton: CRC Press) pp. 151-169.

Weis, W. I., and Drickamer, K. (1994). Trimeric structure of a C-type mannose-binding protein. Structure. 2, 1227-1240.

Yamauchi, T., Kamon, J., Waki, H., Terauchi, Y., Kubota, N., Hara, K., Mori, Y., Ide, T., Murakami, K., Tsuboyama-Kasaoka, N., Ezaki, O., Akanuma, Y., Gavrilova, O., Vinson, C., Reitman, M. L., Kagechika, H., Shudo, K., Yoda, M., Nakano, Y., Tobe, K., Nagai, R., Kimura, S., Tomita, M., Froguel, P., and Kadowaki, T. (2001a). The fat-derived hormone adiponectin reverses insulin resistance associated with both lipoatrophy and obesity. Nat. Med. 7, 941-946.

Yamauchi, T., Waki, H., Kamon, J., Murakami, K., Motojima, K., Komeda, K., Miki, H., Kubota, N., Terauchi, Y., Tsuchida, A., Tsuboyama-Kasaoka, N., Yamauchi, N., Ide, T., Hori, W., Kato, S., Fukayama, M., Akanuma, Y., Ezaki, O., Itai, A., Nagai, R., Kimura, S., Tobe, K., Kagechika, H., Shudo, K., and Kadowaki, T. (2001b). Inhibition of RXR and PPARgamma ameliorates diet-induced obesity and type 2 diabetes. J. Clin. Invest. 108, 1001-1013.

Yamauchi, T., Kamon, J., Ito, Y., Tsuchida, A., Yokomizo, T., Kita, S., Sugiyama, T., Miyagishi, M., Hara, K., Tsunoda, M., Murakami, K., Ohteki, T., Uchida, S., Takekawa, S., Waki, H., Tsuno, N. H., Shibata, Y., Terauchi, Y., Froguel, P., Tobe, K., Koyasu, S., Taira, K., Kitamura, T., Shimizu, T., Nagai, R., and Kadowaki, T. (2003a). Cloning of adiponectin receptors that mediate antidiabetic metabolic effects. Nature. 423, 762-769.

Yamauchi, T., Kamon, J., Waki, H., Imai, Y., Shimozawa, N., Hioki, K., Uchida, S., Ito, Y., Takakuwa, K., Matsui, J., Takata, M., Eto, K., Terauchi, Y., Komeda, K., Tsunoda, M., Murakami, K., Ohnishi, Y., Naitoh, T., Yamamura, K., Ueyama, Y., Froguel, P., Kimura, S., Nagai, R., and Kadowaki, T. (2003b). Globular adiponectin protected ob/ob mice from diabetes and ApoE-deficient mice from atherosclerosis. J. Biol. Chem. 278, 2461-2468.

Yun, D-J., Ibeas, J. I., Lee, H., Coca, M. A., Narasimhan, M. L., Uesono, Y., Hasegawa, P. M., Pardo, J. M., and Bressan, R. A. (1998). Osmotin, a plant antifungal protein, subverts signal transduction to enhance fungal cell susceptibility. Mol. Cell. 1, 807-817.

Yun, D-J., Zhao, Y., Pardo, J. M., Narasimhan, M. L., Damsz, B., Lee, H., Abad, L. R., D'Urzo, M. P., Hasegawa, P. M., and Bressan, R. A. (1997). Stress proteins on the yeast cell surface determine resistance to osmotin, a plant antifungal protein. Proc. Natl. Acad. Sci. USA. 94, 7082-7087.

Zhou, Z. Gartner, A., Cade, R., Ammerer, G. and Errede, B. (1993). Pheromone-induced signal transduction in *Saccharomyces cerevisiae* requires the sequential function of three protein kinases. Mol. Cell. Biol. 13, 2069-2080.

What is claimed is:

1. A method for treating a mammal suffering from disorder selected from the group consisting of type II diabetes, insulin resistance, hyperlipidemia, arteriosclerosis, and heart disease, said method comprising administering to the mammal an isolated PR-5 protein, wherein said type II diabetes, insulin resistance, hyperlipidemia, arteriosclerosis, or heart disease is treated.

2. The method of claim 1, wherein the disorder is type II diabetes.

3. The method of claim 1, wherein the disorder is insulin resistance.

4. The method of claim 1, wherein the disorder is hyperlipidemia.

5. The method of claim 1, wherein the disorder is arteriosclerosis.

6. The method of claim 1, wherein the disorder is heart disease.

7. The method of claim 1, wherein the PR-5 protein is osmotin.

8. The method of claim 1, wherein the PR-5 protein is osmotin.

9. A method for treating a mammalian condition caused by an implicated adiponectin receptor-mediated pathway, said method comprising:
   identifying a mammal suffering from a mammalian condition selected from at least one of type II diabetes, insulin resistance, hyperlipidemia, arteriosclerosis and heart disease; and
   administering osmotin to the mammal,
   wherein said type II diabetes, insulin resistance, hyperlipidemia, arteriosclerosis, or heart disease is treated.

* * * * *

SEQUENCE LISTING

```
<160> NUMBER OF SEQ ID NOS: 3

<210> SEQ ID NO 1
<211> LENGTH: 3033
<212> TYPE: DNA
<213> ORGANISM: Nicotiana tabacum

<400> SEQUENCE: 1
gtcgactttt gtatcagttg atgttctggt agtattacac tagacttagt ttcgtaactg     60
```

-continued

```
attgttttat aaattttccg gtaacgtcca aatatgtcct taccgtcaca tagttggtct      120
atatatccct ttttgaaata gaatccatcc aaattattta gctcttccgt taattatact      180
aaaatgtatg acaaacacta tttccttttt attcagtact ttttttttctt tatcaattta     240 acttgacaaa actcatgaat tcctgttaat tttactatta caggccccac aggttccttc      300
ctgacctgaa ggagatgaaa attatcggag aaatttttttc ggtggtgtta attgggtgaa    360
ggtaggatat gattattcaa attttgaaga tcttgttcct ttcagatctg aagctccaca     420
gtgaacaact ccttcaaaat ctgaataatt atatcctacc ttcaccaaat taacaccacc    480
aaaaaaattt ctccgacaat ttttatctcc ttcttttcag aagaactaga gccttctcgg    540
ttggaaggtt ttggtggtgc aagtttgatt tttaggaata aaatcacgtc aaattggtaa    600
cgaaaatgga gaaggcaccg gaaatggagg aaaccggata tgggagaatg aaaaagggaa    660 aaaagataa gaaagaaaa aagaagaaag aaagagaaa ggtaaagaaa aaagtactaa       720
ataaaaagta gatagtgttt gtaatacact ttaatacaat taaagaaaga gctaattagt    780
ttgggtggat tcattttttaa aaagggcaac tatgtgacgg taaggacata tatggaccaa   840
ctatgtgtat ggtaagggca tatatggacc aattatgtga cggtacgagt atatatgagc    900
taaagtatta acaagggta aatgtgctca atttcgtata ttacaaagcc atatttggac    960
ctttttccgt aaatttatg tagatttaga aaaaagcaac aacctataag gggttggtct    1020
ttaaatattg tcttcatttt ttaatgtact taaagaatga gctctggacc tatatagttc   1080
ttcagagatt tttctattgg atcgctagaa tttatgttat atttattcta cttttattgt    1140
taagtgttca caaattttat tcgattagca tgattttgtg ctagttttat tgttaaacaa   1200
atttcacaga atcggcgtaa ctttattttta tctgcaatcg atgtacttct taaattgttc   1260
attaaatcta cctgactggt ataatttttc tgtgttcttc tctgcgctta ttctacatcc    1320
agaataacga tatctaatta atgagctgct atataaatcg atgtaatagt tctcaaaaag   1380
aaaatgaagg aagaaaaaac tatgtggtgg acaatataa catcatctat atataaaat    1440 taaagtgaaa tccaggattt cagtattaaa actacaggaa aaatttatga tcggtgcaaa   1500
ctccataaaa aatttcggaa gtacaaaatg tggagttcaa actgataaac aaactctaat   1560
aaatttctta taatttttt atattttttgt gacgaatatt attgtttgag ttttattttc   1620
acattaaaaa ctaaatattg aatagcttta aaatgatggc tatctgccaa aaagtggcta  1680
tctgtcaatt tcttgcgaat taaaaaatgg tatagataaa agaaagcaag aaattgacta   1740
aaagagatat tgttacaagt gtcacgttac agagattata ggtcagcgtt attaccaaat   1800
aaattgactt ctatattcat aaaataatta attattaggc ggctcttatg tttaagcgcc    1860
gcctccatct ttgccaaagc atccttgaga tatatccgtt tattagtcaa atgttaataa    1920
atatttatga ttaatatcca tagtacgaaa agccgccatt cccctatata aaccactaaa   1980
caatttgtca ctatatccaa caacccaact tgttaaaaaa aatgtccaac aacatgggca   2040
acttgagatc ttcttttgtt ttcttcctcc ttgccttggt gacttatact tatgctgcca    2100
ctatcgaggt ccgaaacaac tgtccgtaca ccgtttgggc ggcgtcgaca cccataggcg   2160
gtggccggcg tctcgatcga ggccaaactt gggtgatcaa tgcgcacga ggtactaaaa    2220 tggcacgtgt atggggccgt actaattgta acttcaatgc tgctggtagg ggtacgtgcc   2280
aaaccggtga ctgtgtggga gtcctacagt gcaccgggtg gggtaaacca ccaaacacct   2340
tggctgaata cgctttggac caattcagtg gtttagattt ctgggacatt tctttagttg   2400
```

-continued

```
atggattcaa cattccgatg actttcgccc cgactaaccc tagtggaggg aaatgccatg   2460
caattcattg tacggctaat ataaacggcg aatgtccccg cgaacttagg gttcccggag   2520
gatgtaataa cccttgtact acattcggag gacaacaata ttgttgcaca caaggacctt   2580
gtggtcctac atttttctca aaatttttca aacaaagatg ccctgatgcc tatagctacc   2640
cacaagatga tcctactagc acttttactt gccctggtgg tagtacaaat tatagggtta   2700
tcttttgtcc taatggtcaa gctcacccaa attttccctt ggaaatgcct ggaagtgatg   2760
aagtggctaa gtagagtggc tatttctgta ataagatcac cttttggtca aattattcta   2820
tcgacacgtt agtaagacaa tctatttgac tcgtttttat agttacgtac tttgtttgaa   2880
gtgatcaagt catgatcttt gctgtaataa acctaagacc tgaataagag tcacatatgt   2940
atttttgtct tgatgttata tagatcaata atgcatttgg attatcgttt ttatattgtt   3000
tttcttttga agttttagta aagtcttaag ctt                                3033
```

```
<210> SEQ ID NO 2
<211> LENGTH: 738
<212> TYPE: DNA
<213> ORGANISM: Nicotiana tabacum

<400> SEQUENCE: 2
atgggcaact tgagatcttc ttttgttttc ttcctccttg ccttggtgac ttatacttat     60
gctgccacta tcgaggtccg aaacaactgt ccgtacaccg tttgggcggc gtcgacaccc    120
ataggcggtg gccggcgtct cgatcgaggc caaacttggg tgatcaatgc gccacgaggt    180
actaatatgg cacgtgtatg ggccgtact aattgtaact tcaatgctgc tggtaggggt     240
acgtgccaaa ccggtgactg tggtggagtc ctacagtgca ccgggtgggg taaaccacca    300
aacaccttgg ctgaatacgc tttggaccaa ttcagtggtt tagatttctg ggacatttct    360
ttagttgatg gattcaacat tccgatgact ttcgccccga ctaaccctag tggagggaaa    420
tgccatgcaa tccattgtac ggctaatata cggcgaatgt cccgcgaact tagggttccc    480
ggaggatgta ataacccttg tactacattc ggaggacaac aatattgttg cacacaagga    540
ccttgtggtc ctacattttt ctcaaaattt ttcaaacaaa gatgccctga tgcctatagc    600
tacccacaag atgatcctac tagcactttt acttgccctg gtggtagtac aaattatagg    660
gttatctttt gtcctaatgg tcaagctcac ccaaattttc ccttggaaat gcctggaagt    720
gatgaagtgg ctaagtag                                                  738
```

```

<210> SEQ ID NO 3
<211> LENGTH: 246
<212> TYPE: PRT
<213> ORGANISM: Nicotiana tabacum

<400> SEQUENCE: 3

Met Gly Asn Leu Arg Ser Ser Phe Val Phe Phe Leu Leu Ala Leu Val
1               5                   10                  15

Thr Tyr Thr Tyr Ala Ala Thr Ile Glu Val Arg Asn Asn Cys Pro Tyr
            20                  25                  30

Thr Val Trp Ala Ala Ser Thr Pro Ile Gly Gly Gly Arg Arg Leu Asp
        35                  40                  45

Arg Gly Gln Thr Trp Val Ile Asn Ala Pro Arg Gly Thr Lys Met Ala
    50                  55                  60

Arg Val Trp Gly Arg Thr Asn Cys Asn Phe Asn Ala Ala Gly Arg Gly
65                  70                  75                  80
```

```
Thr Cys Gln Thr Gly Asp Cys Gly Gly Val Leu Gln Cys Thr Gly Trp
                85              90              95

Gly Lys Pro Pro Asn Thr Leu Ala Glu Tyr Ala Leu Asp Gln Phe Ser
            100             105             110

Gly Leu Asp Phe Trp Asp Ile Ser Leu Val Asp Gly Phe Asn Ile Pro
            115             120             125

Met Thr Phe Ala Pro Thr Asn Pro Ser Gly Gly Lys Cys His Ala Ile
        130             135             140

His Cys Thr Ala Asn Ile Asn Gly Glu Cys Pro Arg Glu Leu Arg Val
145             150             155             160

Pro Gly Gly Cys Asn Asn Pro Cys Thr Thr Phe Gly Gly Gln Gln Tyr
                165             170             175

Cys Cys Thr Gln Gly Pro Cys Gly Pro Thr Phe Phe Ser Lys Phe Phe
            180             185             190

Lys Gln Arg Cys Pro Asp Ala Tyr Ser Tyr Pro Gln Asp Asp Pro Thr
            195             200             205

Ser Thr Phe Thr Cys Pro Gly Gly Ser Thr Asn Tyr Arg Val Ile Phe
        210             215             220

Cys Pro Asn Gly Gln Ala His Pro Asn Phe Pro Leu Glu Met Pro Gly
225             230             235             240

Ser Asp Glu Val Ala Lys
                245
```